(12) United States Patent
Malinski

(10) Patent No.: US 9,511,196 B2
(45) Date of Patent: Dec. 6, 2016

(54) SYSTEMS AND METHODS FOR PROMOTING WOUND HEALING

(75) Inventor: Tadeusz Malinski, Lancaster, OH (US)

(73) Assignee: Ohio University, Athens, OH (US)

( * ) Notice: Subject to any disclaimer, the term of this patent is extended or adjusted under 35 U.S.C. 154(b) by 1126 days.

(21) Appl. No.: 13/519,595

(22) PCT Filed: Dec. 31, 2010

(86) PCT No.: PCT/US2010/062631
§ 371 (c)(1),
(2), (4) Date: Jun. 28, 2012

(87) PCT Pub. No.: WO2011/082375
PCT Pub. Date: Jul. 7, 2011

(65) Prior Publication Data
US 2012/0296266 A1 Nov. 22, 2012

Related U.S. Application Data

(60) Provisional application No. 61/291,705, filed on Dec. 31, 2009.

(51) Int. Cl.
*A61M 37/00* (2006.01)
*A61M 13/00* (2006.01)
*A61M 35/00* (2006.01)

(52) U.S. Cl.
CPC ............ *A61M 13/003* (2013.01); *A61M 35/00* (2013.01); *A61M 2202/0208* (2013.01); *A61M 2202/0233* (2013.01); *A61M 2202/0275* (2013.01)

(58) Field of Classification Search
CPC ................ A61M 13/003; A61M 35/00; A61M 2202/0208; A61M 2202/0275; A61M 2202/0233
(Continued)

(56) References Cited

U.S. PATENT DOCUMENTS 7,520,866 B2 4/2009 Stenzler et al.
7,762,045 B2 7/2010 Rosati
(Continued)

FOREIGN PATENT DOCUMENTS

WO 9217238 A1 10/1992
WO 03049660 A1 6/2003
(Continued)

OTHER PUBLICATIONS

International Search Report and Written Opinion dated Dec. 14, 2011 pertaining to International Application PCT/US 10/62631.
(Continued)

*Primary Examiner* — Theodore Stigell
(74) *Attorney, Agent, or Firm* — Dinsmore & Shohl LLP

(57) ABSTRACT

In various embodiments, provided are topical gas delivery systems and methods for promoting wound healing. A provided gas delivery system comprises a gas reservoir comprising at least one chamber adapted to contain one or more therapeutic gases selected from NO, CO, $O_2$, air, or combinations thereof, and at least one gas permeable membrane operably coupled to the reservoir. A provided method comprises using a provided gas delivery system to deliver the one or more therapeutic gases to a wound site such that a $NO/ONOO^-$ ratio suitable for promoting wound healing is achieved at the wound site.

21 Claims, 10 Drawing Sheets

(58) Field of Classification Search
USPC .................................................. 604/24–26
See application file for complete search history.

(56) References Cited

U.S. PATENT DOCUMENTS

| | | | |
|---|---|---|---|
| 7,794,438 | B2 | 9/2010 | Henley et al. |
| 8,287,506 | B2 | 10/2012 | Wells et al. |
| 8,722,961 | B2 | 5/2014 | Vinton et al. |
| 2004/0131703 | A1 | 7/2004 | Bach et al. |
| 2006/0200100 | A1 | 9/2006 | Rosati |
| 2007/0065473 | A1 | 3/2007 | Miller |
| 2008/0017194 | A1* | 1/2008 | Hassanein .............. A01N 1/02 128/200.24 |
| 2008/0085329 | A1* | 4/2008 | Roth ................. A61K 31/095 424/701 |
| 2008/0176271 | A1* | 7/2008 | Silver ................. A61B 5/0031 435/29 |
| 2009/0008261 | A1 | 1/2009 | Kotzeva et al. |
| 2010/0081983 | A1 | 4/2010 | Zocher et al. |
| 2010/0272684 | A1 | 10/2010 | Velazquez et al. |
| 2016/0082238 | A1 | 3/2016 | Wells et al. |

FOREIGN PATENT DOCUMENTS

| | | |
|---|---|---|
| WO | 2008/116497 A1 | 10/2008 |
| WO | 2008116497 A1 | 10/2008 |
| WO | 2008116925 A1 | 10/2008 |
| WO | WO2008/116925 * | 10/2008 |
| WO | 2009155689 A1 | 12/2009 |
| WO | WO2009/155689 * | 12/2009 |
| WO | 2011082375 A2 | 7/2011 |
| WO | 2012/035298 A1 | 3/2012 |

OTHER PUBLICATIONS

International Preliminary Report on Patentability dated Aug. 21, 2012 pertaining to International Application PCT/US2010/062631.

European Search Report dated Jul. 24, 2013 pertaining to International Application PCT/US2010062631.

Lewis, Randy S., et al., Kinetics of the Reaction of Nitric Oxide With Oxygen In Aqueous Solutions, 1994 American Chemical Society, Chem. Res. Toxicol, 1994, vol. 7, pp. 568-574, USA.

* cited by examiner

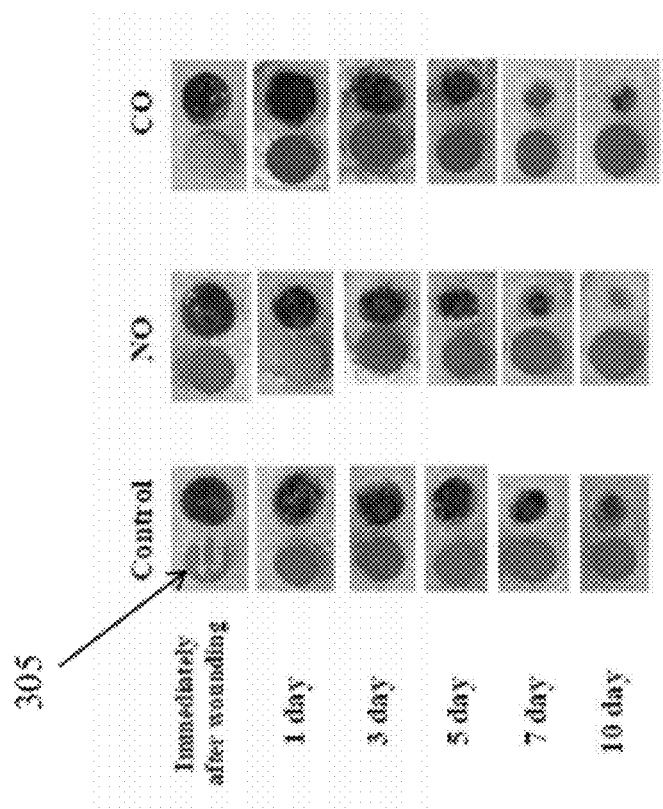

SYSTEMS AND METHODS FOR PROMOTING WOUND HEALING

FIELD

This application relates generally to systems and methods for promoting wound healing by reducing nitroxidative stress in healing wounds, and in particular to systems and methods for delivering one or more therapeutic gases such that a NO/ONOO⁻ ratio suitable for promoting wound healing may be achieved at a wound site.

BACKGROUND

Wound healing is a complex process of cellular and biochemical overlapping events that occurs in four phases—hemostasis, inflammation, proliferation, and remodeling—wherein any delay or failure in one of these phases may lead to impaired healing or failure of a wound to close. The hemostasis phase may be thought of as the initializing step for wound healing. During this phase, damaged blood vessels are essentially sealed by constriction (eventually followed by local vasodilation) and a stable clot is formed to maintain hemostasis. Platelets are activated by collagen from subendothelial layers to change the platelet structure and function, which induces thrombin, fibrin, and hemostatic clot formation.

During the inflammatory phase, the body's immune system response may be characterized by increased vascular permeability, local increase in cytokines and growth factors, attraction and activation of migrating cells. The major goals of the inflammatory phase are to provide for hemostasis and promote removal of cellular, extracellular and pathogen debris. Inflammatory neutrophiles, monocytes, fibroblasts and endothelial cells are recruited to the injury site during this phase. By the third day after an injury, neutrophiles begin to be replaced with activated macrophages, which provide many functions in wound repair, including production of nitric oxide (NO). Enzymes released by macrophages (collagenase and elastase) contribute to debridement of injured tissue, yet a large number of released growth factors stimulate formation of new vessels, chemoattract fibroblasts and induce their proliferation. In acute wounds, the inflammatory stage usually lasts three days. By that time, the absence of any pathogens and devitalized tissue allows the wound to progress to the next phase. In humans with diabetes, reduced activation of inflammatory responses and decreased chemotaxis leads to decline in collagen formation and more subsequent infections. On the other hand a prolonged inflammatory phase may induce hyperproliferative scaring due to increased stimulatory effect of excess released cytokines and growth factors.

During the proliferation phase, epithelialization, neoangiogenesis and collagen deposition by fibroblasts are major components that contribute to formation of granulation tissue. Clinically, pebbled red tissue in the wound base can be seen and can generally involve the replacement of dermal tissues (and sometimes subdermal tissues in deeper wounds) as well as contraction of the wound. Epithelial cells infiltrate to the wound site, where they proliferate and differentiate to form neo-epidermis, thereby providing a protective barrier against infections and fluid loss. The major components of granulation tissue are newly synthesized connective tissue and capillary loops. Fibroblasts, keratinocytes, and endothelial cells collaborate to form new vessels and connective tissue.

The differentiation phase of wound healing begins after termination of cell proliferation and processes associated with the formation of new vessels. The main aspect of this stage of wound repair is the deposition of collagen in the injured site. During this phase, simultaneous synthesis and lysis of extracellular matrix components take place. Macrophages, epidermal cells, and endothelial cells, as well as fibroblasts release several proteomic enzymes such as MMP-1 (collagenase), MMP-2, MMP-9 (gelatinase), MMP-3 (stromelysin) that are involved in old matrix breakdown. In addition, fibroblasts secrete inhibitors TIMP-1 and TIMP-2 that protect matrix synthesis against proteolytic activity of mellatoproteinases. Newly formed collagen is more organized and thicker, providing more tensile support for the connective tissue. An imbalanced ratio between these two groups of components can complicate wound repair. For instance, elevated MMP levels can impair synthesis and deposition of new matrix proteins.

During the complex process of wound healing, gas transmitters are generated within the human body and these can play significant roles in the healing process. Two examples of such gas transmitters are NO and carbon monoxide (CO). NO is generated within the body by nitric oxide synthase (NOS) in the oxidation of L-arginine:

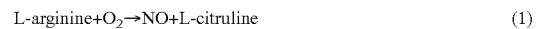

$$\text{L-arginine} + O_2 \rightarrow \text{NO} + \text{L-citruline} \qquad (1)$$

NO can act as a messenger molecule in a wide range of biological processes, such as vascular smooth muscle relaxation, neurotransmission, and inhibition of platelet aggregation. Additionally, NO can play a key role in wound healing by acting as a regulator to control epithelialization, angiogenesis, and collagen deposition. Low levels of NO produced by endothelial NOS (eNOS) and neuronal NOS (nNOS) can be beneficial during the inflammatory phase of wound healing. In contrast, sustained high levels of NO produced by inducible NOS (iNOS) in macrophages may impair wound healing due to oxidation of NO to peroxynitrite (ONOO⁻), which is a cytotoxic molecule associated with apoptosis and necrosis.

NO and ONOO⁻ are among the molecules that can induce heme oxygenase to generate CO within the body:

$$\text{Heme} + O_2 \rightarrow \text{biliverdin} + Fe^{2+} + CO \qquad (2)$$

The generated CO may also play a role in wound healing by activating guanyl cyclase, which leads to smooth muscle relaxation and other vascular effects in tissues. CO can act as a messenger molecule in a wide range of biological systems and is involved in platelet aggregation, neurotransmission processes, protection against oxidative injury and cell death, and it has anti-inflammation activity. CO can influence gene expression in hypoxia, which is a physiological regulator of erythropoiesis, angiogenesis, glycolysis and tissue remodeling. CO can also cause a release of NO from heme that may result in activation of guanylate cyclase.

Oxygen ($O_2$) also has a role as a catalyst and energy source for many cellular functions including maintenance, metabolism and repair. Cells that utilize $O_2$ in the aerobic metabolism of glucose can generate ATP, which can fuel the active cellular process such as the ones during wound healing. Also, $O_2$ can reduce the uncoupling of eNOS and reduce production of superoxide ($O_2^-$) and ONOO⁻, which are the main components of oxidative and nitroxidative stress.

Despite advances in understanding of wound healing, there remains a need for therapeutic devices and/or methods that affect the mechanisms of wound healing, such as vasodilation, inflammation, expression of matrix metalloproteinases, apoptosis, bacterial growth, and collagen deposition. Moreover, there remains a need for improved devices and/or methods of topically treating wounds.

SUMMARY

These needs are at least partially met by the present application, which provides systems and methods for controlled delivery of therapeutic gases to a wound site such that the ratio of $NO/ONOO^-$ in wound tissue is maintained or adjusted to promote wound healing.

In various embodiments, provided are systems for controlled delivery of therapeutic gases to a wound site, comprising (i) a gas reservoir for containing one or more therapeutic gases selected from NO, CO, $O_2$, air, or combinations thereof; and (ii) at least one gas permeable membrane for controlling diffusion of a contained therapeutic gas from the reservoir to the wound site, the at least one gas permeable membrane operably connected to the gas reservoir. The provided system maintains a space between the wound site and the at least one gas permeable membrane when the system is applied to a wound site, and the system delivers, when the system is applied to a wound site, the contained therapeutic gases such that a $NO/ONOO^-$ ratio suitable for promoting wound healing is achieved at the wound site.

In various embodiments, also provided are methods for promoting wound healing, comprising (a) applying a provided gas delivery system to a wound site; and (b) delivering to the wound site, via the gas delivery system, one or more therapeutic gases selected from NO, CO, $O_2$, air, or combinations thereof, for a pre-determined period of time, wherein the one or more therapeutic gases are delivered such that a $NO/ONOO^-$ ratio suitable for promoting wound healing is achieved at the wound site.

BRIEF DESCRIPTION OF THE DRAWINGS

A more complete appreciation of the invention and the many embodiments thereof will be readily obtained as the same becomes better understood by reference to the following detailed description when considered in connection with the accompanying drawings, wherein:

FIG. 10 depicts a comparison of the various stages of healing of a normal excision wound after treatment with therapeutic gases using a gas delivery system.

Figure 1:
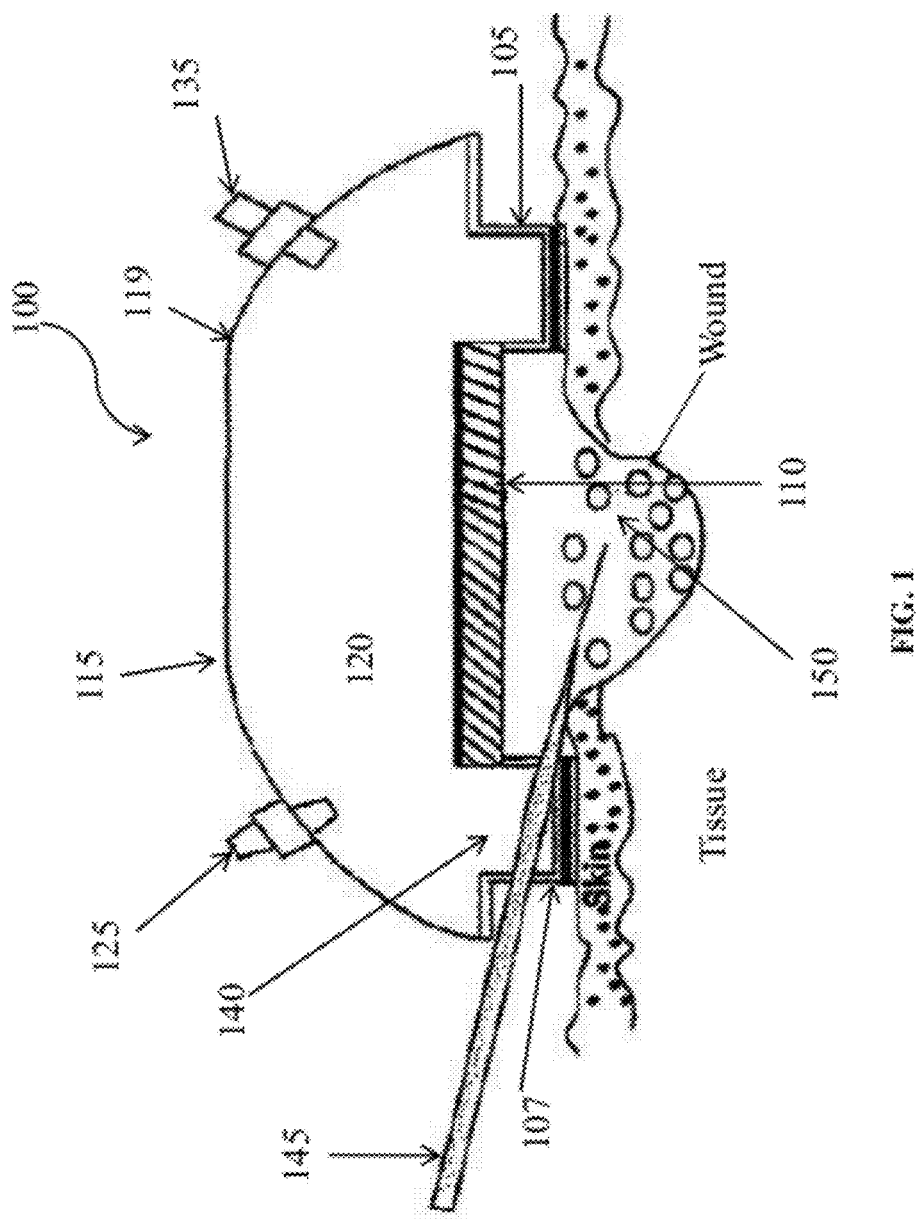
FIG. 1 depicts a side view of an exemplary gas delivery system having a reservoir with a single gas chamber for the controlled supply of therapeutic gases to a wound site.

The provided drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several embodiments of the invention, and together with the description serve to explain the principles of the invention; it being understood, however, that the invention is not limited to the precise arrangements shown.

DESCRIPTION OF EMBODIMENTS

Specific embodiments of the present application will now be described. The invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art. The terminology used in the description herein is for describing particular embodiments only and is not intended to be limiting. As used in the specification and appended claims, the singular forms "a," "an," and "the" are intended to include the plural forms as well, unless the context clearly indicates otherwise.

As used herein, the terms "wound" and "wound tissue" are intended to refer to open wounds (for e.g., incisions, excisions, lacerations, abrasions, punctures, penetrations, etc.) and other such injuries to the skin and surrounding tissue, closed wounds (for e.g., contusions, hematomas, crushing injury, etc.), acute or traumatic wounds, chronic wounds (for e.g., pressure, venous, and diabetic ulcers), and other such injuries to the skin and surrounding tissue, and combinations thereof. Non-limiting examples of a "wound" and "wound tissue" include incisions, burns, and diabetes-related tissue injuries.

As used herein, the term "endogenous" is intended to refer to molecules and molecular processes originating from within the body. Alternatively, the term "exogenous" is intended to refer to molecules and molecular processes originating from outside the body.

Unless otherwise indicated, all numbers expressing quantities of ingredients, properties such as molecular weight, reaction conditions, and so forth as used in the specification and claims are to be understood as being modified in all instances by the term "about." Additionally, the disclosure of any ranges in the specification and claims are to be understood as including the range itself and also anything subsumed therein, as well as endpoints. Unless otherwise indicated, the numerical properties set forth in the specification and claims are approximations that may vary depending on the desired properties sought to be obtained in embodiments of the present invention. Notwithstanding that numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

Wound healing is a complex process of cellular and biochemical overlapping events, and during this complex process, endogenous gas transmitters such as NO, CO, and $O_2$ are generated, and these can play significant roles in the healing process. To better understand such roles, a temporal expression profile of reactive oxygen and reactive nitrogen species [NO, superoxide ($O_2^-$), and $ONOO^-$] as a function of size and depth of various wounds was developed in order to quantify concentrations of NO, CO, $O_2^-$, and $ONOO^-$ in the wounds. Without being bound by theory, it is believed that impaired wound healing (i.e., prolonged, incomplete, or failed healing) can be associated with decreased levels of NO and excessive formation of $ONOO^-$ in wound tissue, as compared to wound tissue undergoing normal healing processes. Further, strong links are believed to exist between NO, CO, and $O_2$ and wound angiogenesis, collagen accumulation and expression of endothelial growth factor. It is also believed that a deficiency of NO due to high oxidative stress inhibits wound healing and that inducible NOS (iNOS) expression increases during wound healing, but endothelial NOS (eNOS) and neuronal NOS (nNOS) become increasingly disarranged such that they generate $O_2^-$ in addition to NO.

In light of the aforementioned, provided herein are systems and methods for promoting wound healing by maintaining or adjusting a NO/$ONOO^-$ ratio at a wound site through topical delivery of one or more therapeutic exogenous gases selected from NO, CO, $O_2$, air, or combinations thereof. In various embodiments, the provided systems comprise (i) a gas reservoir for containing one or more of the therapeutic exogenous gases and (ii) at least one gas permeable membrane for controlling diffusion of a contained therapeutic gas from the reservoir to the wound site, the at least one gas permeable membrane operably connected to the gas reservoir, wherein the system maintains a space between the wound site and the at least one gas permeable membrane when the system is applied to a wound site, and wherein the system delivers, when the system is applied to a wound site, the contained therapeutic gases such that a NO/$ONOO^-$ ratio suitable for promoting wound healing is achieved at the wound site. In various embodiments, the provided methods comprise (a) applying a provided gas delivery system to a wound site; and (b) delivering to the wound site, via the gas delivery system, one or more of the therapeutic exogenous gases for a pre-determined period of time, wherein the one or more therapeutic gases are delivered such that a NO/$ONOO^-$ ratio suitable for promoting wound healing is achieved at the wound site.

Systems

The provided gas delivery systems can maintain an atmosphere of exogenous therapeutic gases in close proximity to wound tissue to promote healing. For example, a gas delivery system may be adapted to deliver therapeutic gases to a wound site in order to combat infection. In other examples, a gas delivery system may be adapted to deliver therapeutic gases to a wound site in order to reduce inflammation. In some examples, a gas delivery system may be adapted to deliver therapeutic gases to a wound site in order to increase vasorelaxation and blood flow, facilitate vascular endothelial growth factor synthesis, and may reduce or inhibit allograft rejection.

The provided gas delivery systems may be adapted to treat various types of wounds. Examples include, but are not limited to, burns, incisions, excisions, lacerations, abrasions, punctures, penetrations, contusions, hematomas, crushing wounds, acute wounds, trauma wounds, chronic wounds, and ulcers.

Diabetes may be associated with reduced NO production due to endothelium dysfunction. One factor that may contribute to endothelial dysfunction is the diminished NO availability due to reduced eNOS expression and scavenging action of reactive oxygen species, mainly $O_2^-$. The impairment of healing in diabetes is very complex and can embrace all phases of wound healing, including inflammation, proliferation, matrix formation and angiogenesis. Accordingly, in some examples, a provided gas delivery system may be adapted to deliver therapeutic gases to a wound site(s) of a person suffering from diabetes such that a NO/$ONOO^-$ ratio suitable for promoting wound healing is achieved.

Wound healing in burn tissue can be impaired due to acute overproduction of inflammatory active substances. The triggered inflammatory reaction can result in several inflammatory mediators that may interfere with the actions of NO. The NO may turn into a proinflammatory and cytotoxic agent, such as $ONOO^-$, which can impair wound healing by triggering inflammation, edema, apoptosis and necrosis of tissue. Accordingly, in some examples, a provided gas delivery system may be adapted to deliver therapeutic gases to a wound site(s) of a burn victim such that a NO/$ONOO^-$ ratio suitable for promoting wound healing is achieved.

The provided gas delivery systems may be adapted to fit wounds of various type, size and shape, and severity. For example, a gas delivery system may be adapted to treat small wounds, as well as large wounds. In some examples, a gas delivery system may also be adapted to fit all or a portion of a head, chest, torso, arm, hand, leg, or foot of a body. In some examples, a gas delivery system may be incorporated into a wearable article that may be used to deliver therapeutic gases to the surface of a wound site. Examples of wearable articles may include, but are not limited to, dressings, bandages, tapes, clothing, gloves, hats, patches, sleeves, and wraps.

In various embodiments, the provided gas delivery systems may generally comprise a gas reservoir comprising at least one chamber. Thus, the reservoir may have one, two, three, or more chambers for containing one or more therapeutic gases. In some embodiments, the gas reservoir comprises at least two chambers, and the gas reservoir is adapted to maintains a separation of gas contained in the first chamber from gas contained in the second chamber. Similarly, where the gas reservoir comprises three or more chambers, the gas reservoir may be adapted to maintain a separation of gas contained in the first chamber from gas contained in the second chamber and from gas contained in the third chamber.

In the various embodiments, the system may also generally comprise at least one gas permeable membrane for controlling diffusion of therapeutic gases contained in the gas reservoir to the wound site. Said at least one gas permeable membrane may be operably connected to the gas reservoir. In some embodiments, the system comprises at least two gas permeable membranes. For example, the system may comprise a first and a second gas permeable membrane, the first of which is operably connected to a first chamber of the reservoir, and the second of which is operably connected to a second chamber of the reservoir.

In the various embodiments, the gas delivery system may be adapted to be applied to or otherwise disposed over the wound site, whereby a gap is created or otherwise maintained between the wound site and the at least one gas permeable membrane. Without wishing to be bound by theory, it is believed that such a gap may serve to prevent the gas delivery system from binding with tissue within the wound so that upon removal of the gas delivery system from a wound site, there is no or minimal tissue loss at the wound site. Tissue removal can lead to pain and can retard the healing process. The provided gas delivery system, when applied to a mammal (including but not limited to humans), delivers therapeutic gases such that a NO/ONOO⁻ ratio suitable for promoting wound healing is achieved at the wound site. In some embodiments, this ratio may be pre-determined. In some embodiments, this ratio may be determined during treatment. In some embodiments, this ratio may be pre-determined, but modified during treatment.

In some embodiments, a provided gas delivery system may also comprise one or more gaskets for sealing the gas delivery system against the skin surrounding a wound. The one or more gaskets may be operably connected to the at least one gas permeable membrane, the gas reservoir, or both. Suitable gaskets are of a material of construction that is flexible for interface with the skin and that provides a substantially gas tight seal. Examples of gasket material include, but are not limited to, polyethylene and polypropylene. The gasket opening size and shape can be enlarged or reduced depending on the size of a wound. In some examples, one or more portions of gaskets may be attached to one or more portions of the gas delivery system surrounding at least a portion of a membrane, wherein and one or more portions of the gaskets are sealed against the surface of the skin.

In some embodiments, a provided gas delivery system may comprise one or more gas ports adapted to supply therapeutic gases to the at least one chamber of the reservoir when connected to a therapeutic gas source, to remove a contained therapeutic gas from the at least one chamber of the gas reservoir, or both. The one or more gas ports may be operably connected to the at least one chamber.

In some embodiments, a provided gas delivery system may comprise one or more additional ports, said ports providing access to the interior of the gas delivery system and may permit insertion of one or more sensors (such as sensors that monitor exogenous gas and generated particle concentrations at the wound site), permit sampling of tissue or body fluids from the wound, or permit other operations within the gas delivery system's interior.

As described, a provided gas delivery system may comprise a gas reservoir having more than one chamber. A multi-chamber system can allow for the separate delivery of one or more therapeutic gases (or combination of gases) from the delivery of another therapeutic gas or gas combination. A multi-chamber system may be advantageous, for example, where reactions between gases would either hinder their effectiveness or result in the creation of toxic conditions. For example, $O_2$ and NO can react in the gaseous phase to produce toxic $NO_2$, and the rate of reaction is much faster if the gases diffuse through a shared membrane, thereby generating potentially dangerous amounts of toxic $NO_2$. The multi-chamber design can allow for segregation of $O_2$ and NO, thereby allowing for delivery of both to a wound site while minimizing the opportunity for reaction between the gases and formation of toxic $NO_2$. A multi-chamber system may also be advantageous where controlled delivery of different gases at different rates, in varied sequences, and other manners of control are desirable.

In various embodiments, suitable gas delivery systems may comprise one or more chambers having a volume that is suitable for the wound site being treated. For example, the chamber volume may be from less than about 1 cm³ to about 3 L. The chamber volume may also be of about 0.5-1 cm³, 1-1.5 cm³, 1.5-2 cm³, 2-2.5 cm³, 2.5-3 cm³, 3-3.5 cm³, 3.5-4 cm³, 4-4.5 cm³, 4.5-5 cm³, 5-5.5 cm³, 5.5-6 cm³, 6-6.5 cm³, 6.5-7 cm³, 7-7.5 cm³, 7.5-8 cm³, 8-8.5 cm³, 8.5-9 cm³, 9-9.5 cm³, 9.5-10 cm³; 10-50 cm³, 50-100 cm³, 100-150 cm³, 150-200 cm³, 200-250 cm³, 250-300 cm³, 300-350 cm³, 350-400 cm³, 400-450 cm³, 450-500 cm³, 500-550 cm³, 550-600 cm³, 600-650 cm³, 650-700 cm³, 700-750 cm³, 750-800 cm³, 800-850 cm³, 850-900 cm³, 900-950 cm³, 950-1000 cm³; 1 L (1000 cm³)-1.5 L, 1.5 L-2 L, 2 L-2.5 L, 2.5 L-3 L, and combinations thereof. In one example, a chamber has a rectangular opening of about 1 cm length and about 4 mm width, and a volume of about 10-500 cm³.

Figure 2:
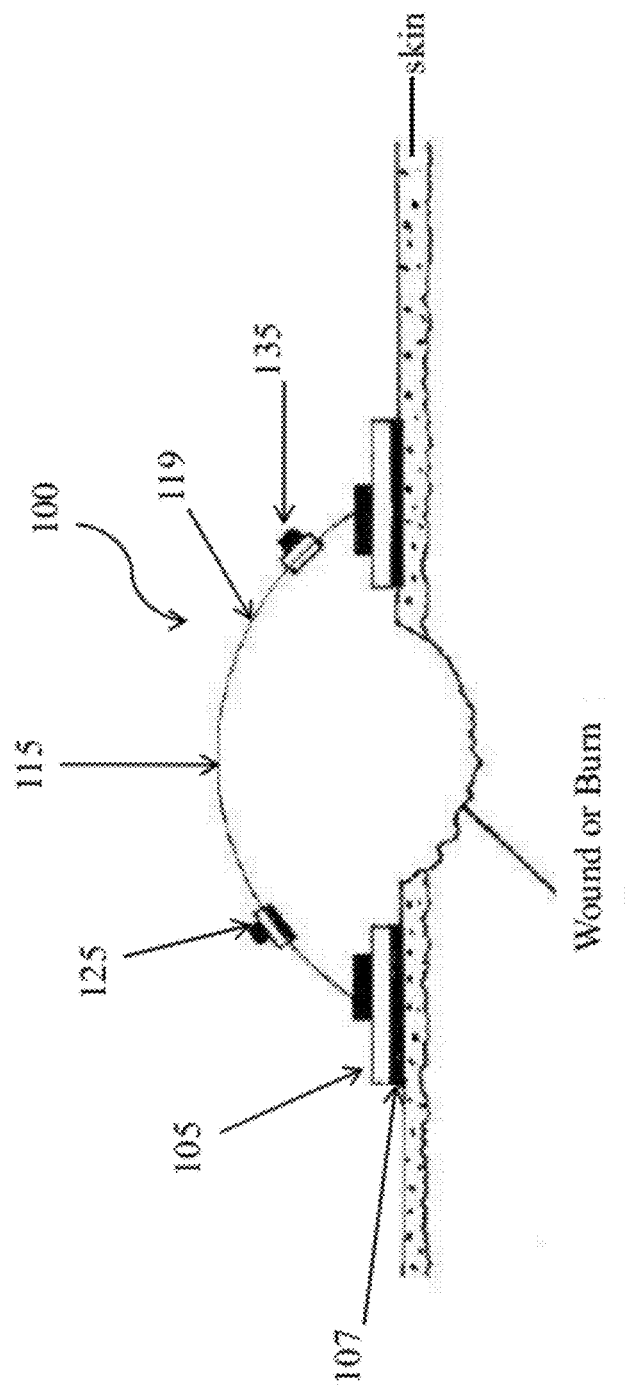
FIG. 2 depicts a side view of an exemplary gas delivery system having a reservoir with a single gas chamber for the supply of therapeutic gases to a wound site.
Figure 3:
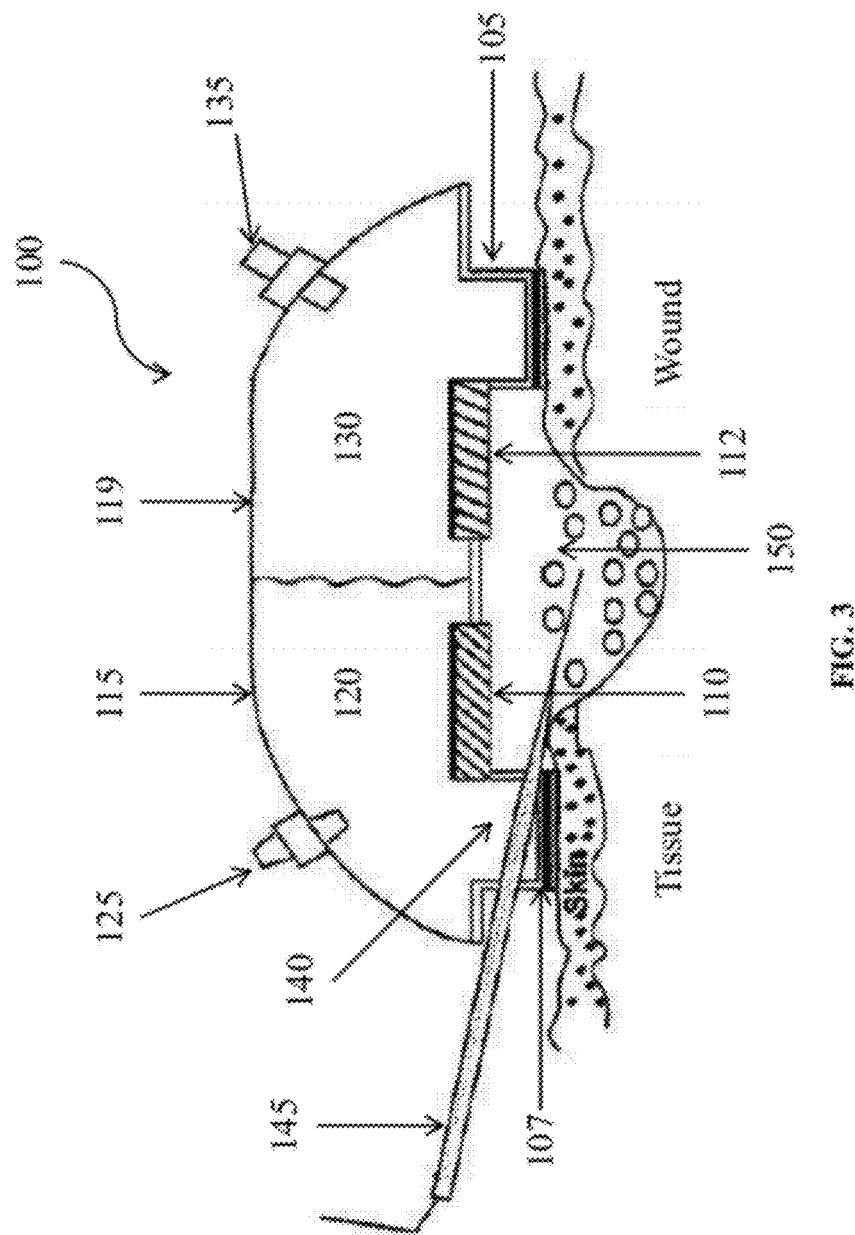
FIG. 3 depicts a side view of an exemplary gas delivery system having a reservoir with two gas chambers for the controlled supply of therapeutic gases to a wound site.
Figure 4:
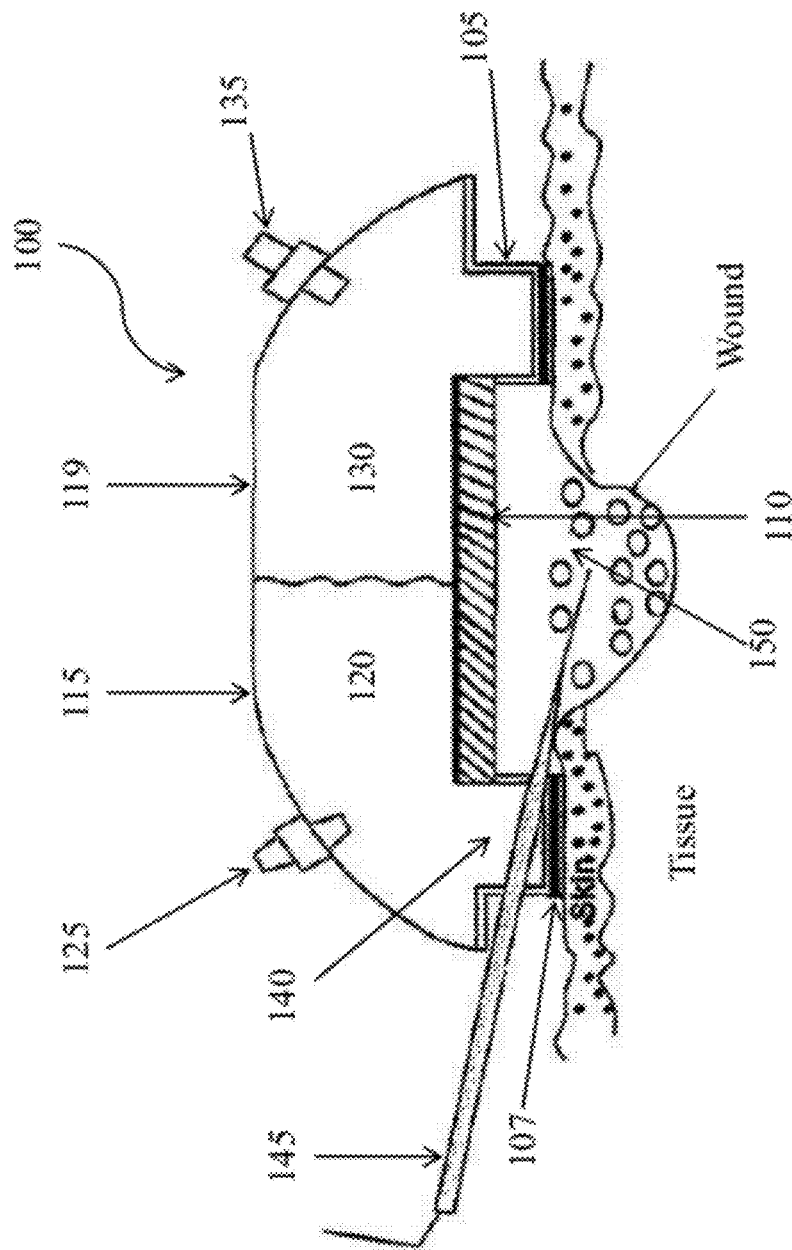
FIG. 4 depicts a side view of an exemplary gas delivery system having a reservoir with two gas chambers and a single gas permeable membrane for the controlled supply of therapeutic gases to a wound site.
Figure 5:
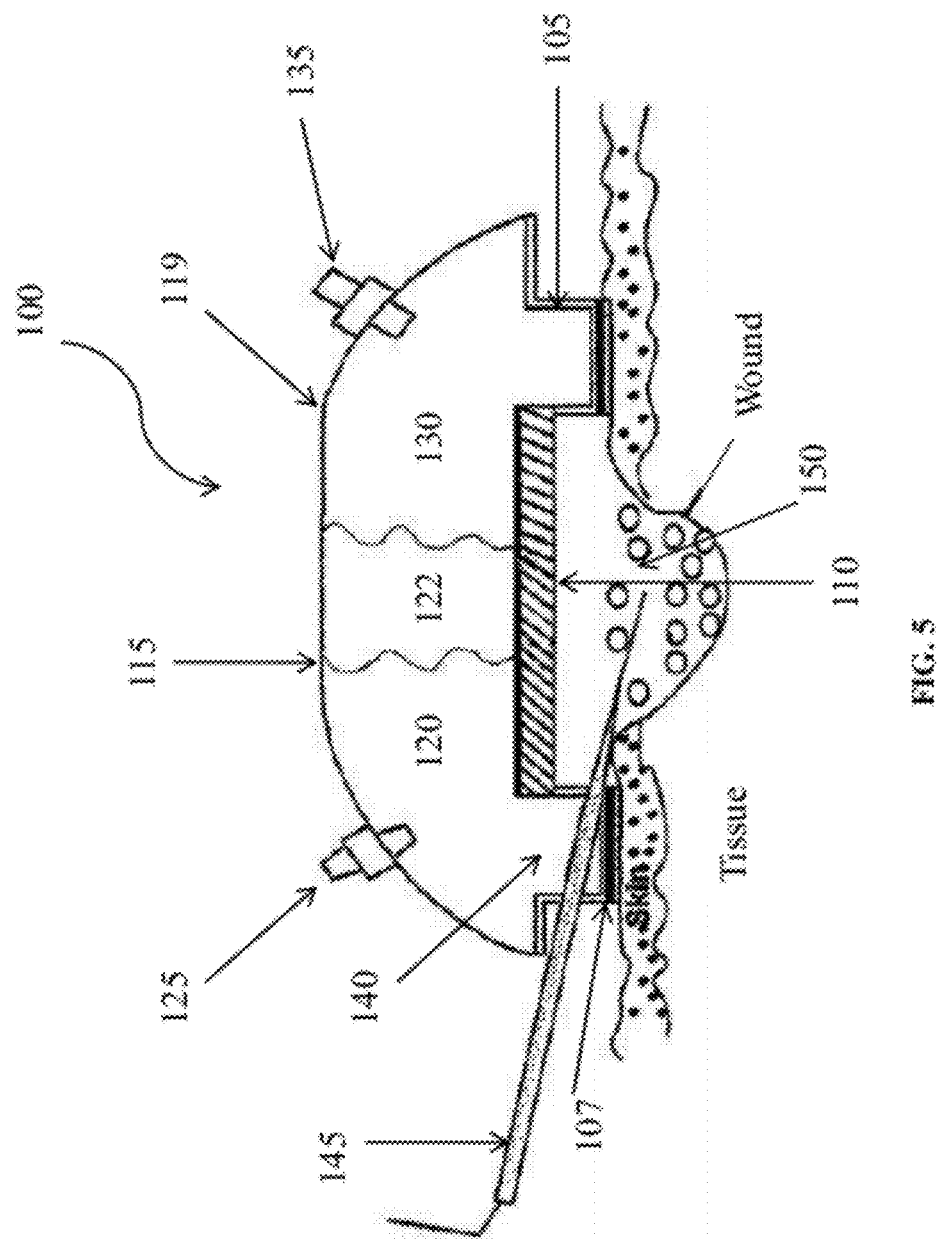
FIG. 5 depicts a side view of an exemplary gas delivery system having a reservoir with three gas chambers for the controlled supply of therapeutic gases to a wound site.
Figure 6:
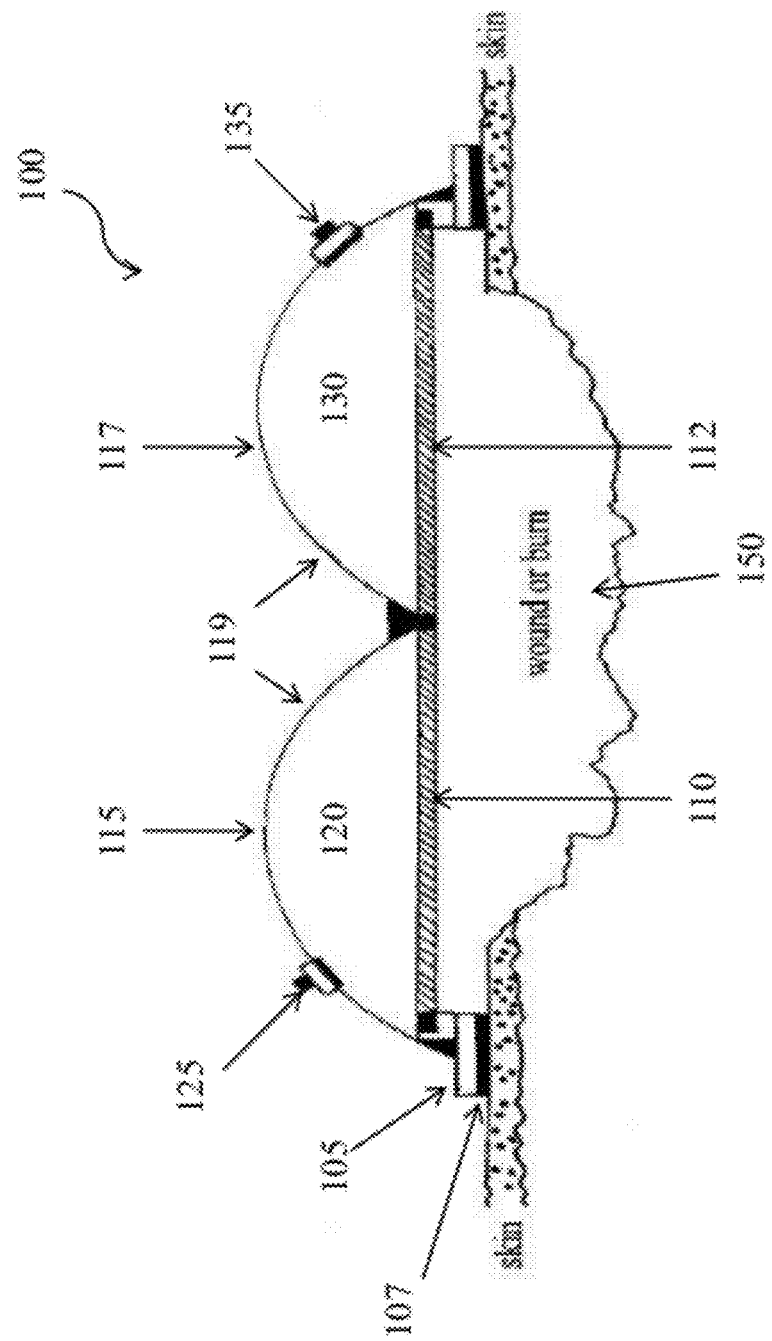
FIG. 6 depicts a side view of an exemplary gas delivery system for the controlled supply of therapeutic gases to a wound site.

Exemplary gas delivery systems are depicted in FIGS. 1-6. Referring to FIG. 1, a gas delivery system 100 for supplying one or more therapeutic gases to a wound site in order to achieve a pre-determined NO/ONOO⁻ ratio at the wound site is depicted. The gas delivery system 100 includes a gasket 105 adhered to skin with an adhesive 107, a gas permeable membrane 110, a gas impermeable member 115, and a gas reservoir 119 comprising a chamber 120. Also depicted is a first gas port 125, a second gas port 135 and port 140 for providing access to the wound site or system interior. The gas impermeable member 115 may be a material of construction of the reservoir 119, or the reservoir may otherwise comprise a gas impermeable member 115. In some embodiments, the gasket 105 may be operably coupled to a gas permeable membrane 110 and gas impermeable member 115, which together may form a chamber 120. The gas delivery system 100 may be without a gas permeable membrane as depicted in FIG. 2. In FIG. 3, depicted is a gas delivery system 100 that includes a gasket 105 adhered to skin with an adhesive 107, a first gas permeable membrane 110, a second gas permeable membrane 112 a gas reservoir 119 comprising a first chamber 120 and a second chamber 130. Also depicted is a first gas port 125, a second gas port 135, and a port 140 for providing access to a wound or interior of the system. As shown, gasket 105 is operably coupled to a first gas permeable membrane 110, a second gas permeable membrane 112, and gas impermeable member 115. In FIG. 4, depicted is a gas delivery system 100 that includes a gasket 105 adhered to skin with an adhesive 107, a gas permeable membrane 110, a gas reservoir 119 comprising a first chamber 120 and a second chamber 130. Also depicted is a first gas port 125, and a second gas port 135, and a port 140 for providing access to a wound or interior of the system. As shown, gasket 105 is operably coupled to a gas permeable membrane 110 and gas impermeable member 115. In FIG. 5, depicted is a gas delivery system 100 that includes a gasket 105, a gas permeable membrane 110 and a gas reservoir 119 comprising a gas impermeable member 115, a first chamber 120, a second chamber 122, and a third chamber 130. Also depicted is a first gas port 125, a second gas port 135 and port 140 for access to a wound or interior of the system. As shown, gasket 105 is operably coupled to a gas permeable membrane 110 and gas impermeable member 115. In FIG. 6, depicted is a gas delivery system 100 that includes a gasket 105, a first gas permeable membrane 110, a second gas permeable membrane 112, a first gas impermeable member 115, a second gas impermeable member 117, and a gas reservoir 119 comprising a first chamber 120 and a second chamber 130. Also depicted is a first gas port 125 and a second gas port 135. As shown, gasket 105 is operably coupled to a first gas permeable membrane 110, a second gas permeable membrane 112, a first chamber 120 a second chamber 130, and the gas reservoir 119.

In the various examples, gasket 105 may be adapted to surround the wound site and adhere the gas delivery system 100 comprising one or more chambers 120, 122 and 130 to healthy skin surrounding the wound site. The adhered gasket 105 provides a seal to prevent gas leakage and contain gas topically diffused to the wound site. Adhering to skin may be enhanced with the aid of an adhesive 107 (either hypoallergenic or non-hypoallergenic), a sealing gel, tape, or other suitable bonding material. One of skill in the art will appreciate that adhering may be done by a variety of other means that may be used to secure a gas delivery system 100 over the wound site.

Operable coupling of the various components may be achieved in any manner, such as using adhesives, thermal sealing, stitching, and/or any combination of techniques may be used to achieve strong bonds that resist leaking and bursting when one or more chambers 120, 122 and 130 are filled with gas. The gasket 105 may also be configured to be coupled to the one or more gas permeable membranes 110, 112. The one or more gas permeable membranes 110, 112 are adapted to overlie the wound site and allow diffusion of the gases to the wound site. The one or more gas impermeable portions 115, 117 of the reservoir are depicted overlying the one or more gas permeable membranes 110, 112. The one or more chambers 120, 122 and 130 may, in some embodiments, be formed from flexible elastic materials that are inflatable over the wound site, such as that shown in FIGS. 1-5. Alternatively, the one or more chambers 120, 122 and 130 of gas delivery system 100 may be formed as a rigid structure from suitable materials. Examples of rigid materials include, but are not limited to, rigid plastics.

The first and second gas permeable membranes 110, 112 depicted in FIGS. 3 and 6 are separate membranes provided for separate chambers. Alternatively, a single gas permeable membrane 110 may be used, which is shared between two or more chambers as shown in FIGS. 4 and 5. In the various examples, suitable gas permeable membranes 110, 112 may be constructed from materials that are permeable to one or more gases. In some examples, the gas permeable membranes 110, 112 may include a selectively permeable membrane. In some examples, the gas permeable membranes 110, 112 may include numerous combinations of materials. For example, in some examples, the first gas permeable membrane 110 may include a NO permeable material and the second gas permeable membrane 112 may include a NO impermeable material. In some examples, a single gas permeable membrane 110 may include a NO impermeable material that is coupled to a NO permeable material.

Examples of suitable gas permeable materials for use in membranes include, but are not limited to, 2-methacryloyloxyethyl phosphorylcholine copolymers, 2-methacryloyloxyethyl phosphorylcholine copolymers covered with methacrylate coating (to reduce protein absorption), polymethylsiloxane, FEP (fluorinated ethylene-propylene), teflon, polyacetylenes with bulky substituents (eg., 2-octyne, 2-decyne or larger substituents), Nafion, nonthrombogenic membranes like polyethylene porous membrane modified with phospholipide polymers, and combinations thereof. In some examples, suitable membranes are nonthrombogenic membranes. In some examples, suitable gas permeable membranes may also allow for some permeability to water vapor to prevent both excessive dehydration as well as buildup of exudate. For example, a suitable membrane may have a water vapor permeability of at least about 300 g/m$^2$. Of course, various other suitable materials may be apparent to those of ordinary skill in the art in view of the teachings herein.

One or more gas impermeable members 115, 117 of a gas reservoir 119 may be substantially impermeable to one or more gases, and may be arranged and/or configured to limit a loss of a concentration of one or more of gases during release in the gas delivery system 100. The one or more gas impermeable members 115, 117 may be constructed from flexible sheet materials that can take on a variety of shapes. In some examples, the one or more gas impermeable members 115, 117 may have a rectangular configuration as shown in FIGS. 1-6. In some examples, the one or more gas impermeable members 115, 117 can be a bag to surround a limb or to wrap around a limb. In some examples, the one or more gas impermeable members 115, 117 may be constructed from rigid materials.

Examples of suitable gas impermeable materials include, but are not limited to, metalized polymeric film, or a metallic film, such as an aluminum film, plastics, such as polyethylene, polyurethane, polyesters, polyamides, polyethers, polycarbonates, polyacrylonitrile, polystyrene, polypropylene, poly(acrylic acid) polyethylene, polyvinylacetates, polyvinylalcohol, polystyrene, polyethers, polycarbonates, polyamides, polyolefins, and combinations thereof. Of course, various other suitable materials may be apparent to those of ordinary skill in the art in view of the teachings herein. In some examples, the impermeable material may be transparent.

The size, shape, and thickness of the one or more gas permeable or impermeable materials can be varied depending upon the application. In one example, a suitable gas permeable or impermeable material may have a circular, oval, square, triangular, or rectangular shape. In another example, a suitable gas permeable or impermeable material may have an area that is about 1-30 times the size of the wound, wherein the area of the gas permeable or impermeable material may be about 1-5%, 5-10%, 10-15%, 15-20%, 20-25%, 25-30% larger than the area of the wound. Good results have been obtained with gas permeable or impermeable materials having an area of about 0.5-40 cm$^2$. In a further example, a suitable gas permeable or impermeable material may have a thickness of less than about 1 µm to about 300 mm, wherein thickness may be about 1-50 µm, 50-100 µm, 100-150 µm, 150-200 µm, 200-250 µm, 250-300 µm, 300-350 µm, 350-400 µm, 400-450 µm, 450-500 µm, 500-550 µm, 550-600 µm, 600-650 µm, 650-700 µm, 700-750 µm, 750-800 µm, 800-850 µm, 850-900 µm, 900-1000 µm; 1 mm (1000 µm)-25 mm, 25-50 mm, 50-75 mm, 75-100 mm, 100-125 mm, 125-150 mm, 150-175 mm, 175-200 mm, 200-225 mm, 225-250 mm, 250-275 mm, 275-300 mm, and combinations thereof. Good results have been obtained with gas permeable or impermeable material having a thickness of about 80 µm.

Figure 7:
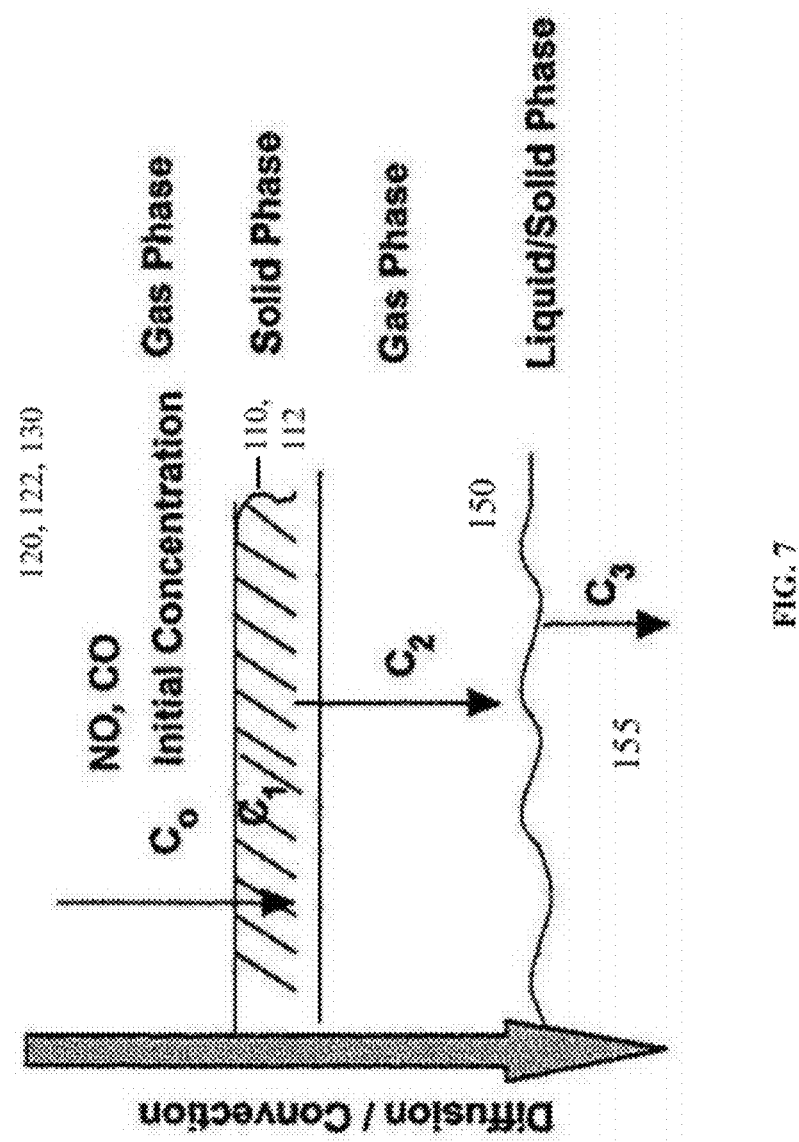
FIG. 7 depicts diffusion and convection processes involved in delivery of therapeutic gases to a wound site using a gas delivery system.

Controlled release of the one or more therapeutic gases through one or more gas permeable membranes 110, 112 to a wound site 155 is depicted in FIG. 7. The gases are delivered to a wound site 155 from a chamber 120, 122, 130 of a gas delivery system based on diffusion and convection processes. The amount of contained gas released to the wound site 155 may vary according to the concentration of the gas, the material used as the gas permeable membrane, temperature, atmospheric pressure, or other factor. As shown, one or more therapeutic gases present at an initial concentration (C0) within the reservoir diffuse through a gas permeable membrane 110 to the wound site 155. A concentration gradient will exist in the gas permeable membrane 110 as the one or more therapeutic gases diffuse through. The average gas permeable membrane 110 concentration is shown as C1. The gas permeable membrane 110, 112 concentration (C1) can vary and depends on a variety of factors including, but not limited to, membrane thickness, membrane area, and diffusion coefficient of the membrane. One or more therapeutic gases exiting the gas permeable membrane 110, 112 may have a concentration (C2) present in a gap 150 above the wound site 155. The one or more therapeutic gases are then absorbed into the wound site 155 at a concentration of C3.

In one example, permeation of gaseous NO through a gas permeable membrane can enable a constant NO delivery rate that allows for steady-state NO concentrations above the wound site (C2) and within wound tissue (C3), even in the presence of species that react with NO (for example, oxygen). In order to establish a steady-state, physiologically relevant NO concentration in the wound (C3), the NO concentration in the gas delivery system (C0) has to be higher than in the gas permeable membrane (C1) and the gap (C2).

In some examples, NO concentration in the wound (C3) in normal tissue (e.g., endothelial cells, smooth muscles, etc.) may be about 1-50 nmol/L, wherein the NO concentration in the wound C3 may be about 5-10, 10-15, 15-20, 20-25, 25-30, 30-35, 35-40, 40-45, 45-50 nmol/L, and combinations thereof. In some examples, the NO concentration in the wound C3 in hypoxic tissue (e.g., wounds, burns, etc.) may be less than about 1 nmol/L. In some examples, the NO concentration in the wound C3 in wound tissue treated with therapeutic gases may be about 5-90 nmol/L, wherein the NO concentration in the wound C3 may be about 5-10, 10-15, 15-20, 20-25, 25-30, 30-35, 35-40, 40-45, 45-50, 50-55, 55-60, 60-65, 65-70, 70-75, 75-80, 80-85, 85-90 nmol/L, and combinations thereof.

In some examples, $O_2$ concentration in the wound (C3) in normal tissue may be about $P_{O_2}$=5-113 KPa (40-100 mmHg), wherein the $O_2$ concentration in the wound C3 may be about 40-45, 45-50, 50-55, 55-60, 60-65, 65-70, 70-75, 75-80, 80-85, 85-90, 90-95, 95-100 mmHg, and combinations thereof. In some examples, the $O_2$ concentration in the wound C3 in hypoxic tissue may be about $P_{O_2}$=0.5-25 KPa (4-20 mmHg), wherein the $O_2$ concentration in the wound C3 may be about 4-5, 5-6, 6-7, 7-8, 8-9, 9-10, 10-11, 11-12, 12-13, 13-14, 14-15, 15-16, 16-17, 17-18, 18-19, 19-20 mmHg, and combinations thereof. In some examples, the $O_2$ concentration in the wound C3 in wound tissue treated with therapeutic gases may be about $P_{O_2}$=3-80 KPa (24-78 mmHg), wherein the $O_2$ concentration in the wound C3 may be about 24-26, 26-28, 28-30, 30-32, 32-34, 34-36, 36-38, 38-40, 40-42, 42-44, 44-46, 46-48, 48-50, 50-52, 52-54, 54-56, 56-58, 58-60, 60-62, 62-64, 64-66, 66-68, 68-70, 70-72, 72-74, 74-76, 76-78 mmHg, and combinations thereof.

In some examples, CO concentration in the wound (C3) in normal tissue may be less than about 1 nmol/L. In some examples, the CO concentration in the wound C3 in hypoxic tissue may be about 1-30 nmol/L, wherein the CO concentration in the wound C3 may be about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30 nmol/L, and combinations thereof. In some examples, the CO concentration in the wound C3 in wound tissue treated with therapeutic gases may be about 25-90 nmol/L, wherein the CO concentration in the wound C3 may be about 25-30, 30-35, 35-40, 40-45, 45-50, 50-55, 55-60, 60-65, 65-70, 70-75, 75-80, 80-85, 85-90 nmol/L, and combinations thereof.

The delivered therapeutic gases may diffuse into wound tissue to restore the NO/ONOO— ratio at a wound site and maintain or improve wound healing. In some examples, the gas delivery system may provide a controlled supply of exogenous NO, CO, air, $O_2$, or combinations thereof to a wound site. The exogenous therapeutic gases may be delivered to the wound site to promote wound healing by maintaining the natural or adjusting the NO/ONOO⁻ ratio in wound tissue. In some examples, the exogenous therapeutic gases may be delivered to the wound site to increase the NO/ONOO⁻ ratio in wound tissue. In use, exogenous therapeutic gases may be delivered to a wound under normal or near normal atmospheric pressure (approx. 1 atm), or under elevated pressure (>1 atm).

Referring to FIGS. 1 and 2, the chamber 120 may contain a therapeutic gas selected from NO, CO, air, $O_2$, or combinations thereof. Referring to FIGS. 3, 4 and 6, the first chamber 120 may contain a first therapeutic gas selected from NO, CO, or combinations thereof. The second chamber 130 may contain a second therapeutic gas selected from air, $O_2$, CO, or combinations thereof. Referring to FIG. 5, the first chamber 120 may contain a first therapeutic gas selected from NO. The second chamber 122 may contain a second therapeutic gas selected from CO. The third chamber 130 may contain a third therapeutic gas selected from air or $O_2$.

Related to FIGS. 3, 4 and 6, in one example, the first and second chamber 120, 130 may be configured to separate the delivery of air or oxygen from the delivery of NO. In another example, the first and second chamber 120, 130 may be configured to separate the delivery of air or oxygen from the delivery of CO. In yet another example, the first and second chamber 120, 130 may be configured to separate the delivery of CO from the delivery of NO. In yet another example, the first and second chamber 120, 130 may be configured to separate the delivery of air or oxygen from the delivery of a mixture of CO and NO. In some examples, the gas delivery system 100 may be used to deliver a mixture of gases to the wound, wherein such mixture is separately delivered, either simultaneously or in series, from another gas or gas mixture. For example, a mixture of CO and NO may be delivered to the wound simultaneously or in series with oxygen. In another example, a mixture of CO and $O_2$ may be delivered to the wound simultaneously or in series with NO. Of course, other combinations of gases may be apparent to those of ordinary skill in the art in view of the teachings herein.

The oxygen may be pure oxygen. The air may comprise varying levels of oxygen. For example, air may comprise at least 21% oxygen. In some examples, NO may be contained within the reservoir or delivered to the wound site at concentrations (C0, C1, or C2) of from about 50 ppm to about 1000 ppm for treatment times ranging from between about 15 minutes to about 30 mins. In some examples, NO may be contained or delivered at a concentration of from about 500 ppm to about 1000 ppm for treatment times ranging from between about 15 minutes to about 30 mins. In some examples, NO may also be contained or delivered at a concentration of about 50-75, 75-100, 100-125, 125-150, 150-175, 175-200, 200-225, 225-250, 250-275, 275-300, 300-325, 325-350, 350-375, 375-400, 400-425, 425-450, 450-475, 475-500, 500-525, 525-550, 550-575, 575-600, 600-625, 625-650, 650-675, 675-700, 700-725, 725-750, 750-775, 775-800, 800-825, 825-850, 850-875, 875-900, 900-925, 925-950, 950-975, 975-1000 ppm, and combinations thereof for treatment times ranging from between about 15 minutes to about 30 mins.

In some embodiments, NO may be present at concentrations from about 50 ppm to about 250 ppm for treatment times ranging from between about 15 minutes to about 3 hours. In some examples, NO may be present at a concentration of from about 100 ppm to about 200 ppm for treatment times ranging from between about 15 minutes to about 3 hours. In some examples, NO may also be present at a concentration of about 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250 ppm, and combinations thereof for treatment times ranging from between about 15 minutes to about 3 hours.

In some embodiments, CO may be present at a concentration of from about 100 ppm to about 250 ppm for treatment times ranging from between about 20 minutes to about 30 mins. In some examples, CO may be contained within the reservoir or delivered to the wound site at concentrations (C0, C1, or C2) of from about 150 ppm to about 200 ppm for treatment times ranging from between about 15 minutes to about 30 mins. In some examples, CO may also be contained or delivered at a concentration of about 100-110, 110-120, 120-130, 130-140, 140-150, 150-160, 160-170, 170-180, 180-190, 190-200, 200-210, 210-220, 220-230, 230-240, 240-250 ppm, and combinations thereof for treatment times ranging from between about 15 minutes to about 30 mins.

In some embodiments, CO may be present at a concentration of from about 50 ppm to about 200 ppm for treatment times ranging from between about 30 minutes to about 3 hours. In some examples, CO may be contained within the reservoir or delivered to the wound site at concentrations (C0, C1, or C2) of from about 100 ppm to about 175 ppm for treatment times ranging from between about 30 minutes to about 3 hours. In some examples, CO may also be contained or delivered at a concentration of about 50-55, 55-60, 60-65, 65-70, 70-75, 75-80, 80-85, 85-90, 90-95, 95-100, 100-105, 105-110, 110-115, 115-120, 120-125, 125-130, 130-135, 135-140, 140-145, 145-150, 150-155, 155-160, 160-165, 165-170, 170-175, 175-180, 180-185, 185-190, 190-195, 195-200 ppm, and combinations thereof for treatment times ranging from between about 30 minutes to about 3 hours.

In some examples, the first therapeutic gas may be NO contained or delivered at a concentration of from about 50 ppm to about 1000 pm, and the second therapeutic gas may be CO contained or delivered at a concentration of from about 100 ppm to about 250 ppm. In some examples, the first therapeutic gas may be NO contained or delivered at a concentration of from about 50 ppm to about 250 ppm, and the second therapeutic gas may be CO contained or delivered at a concentration of from about 50 ppm to about 200 ppm.

In some examples, the first therapeutic gas may be NO contained or delivered at a concentration of from about 500 ppm to about 1000 pm, and the second therapeutic gas may be CO contained or delivered at a concentration of from about 100 ppm to about 250 ppm. In some examples, the first therapeutic gas may be NO contained or delivered at a concentration of from about 800 ppm to about 1000 ppm, and the second therapeutic gas may be CO contained or delivered at a concentration of from about 150 ppm to about 250 ppm.

In some examples, the first therapeutic gas may be NO contained or delivered at a concentration of from about 50 ppm to about 1000 pm, and the second therapeutic gas may be air containing about 21% $O_2$ or pure $O_2$. In some examples, the first therapeutic gas may be NO contained or delivered at a concentration of from about 50 ppm to about 250 ppm, and the second therapeutic gas may be air containing about 21% $O_2$ or pure $O_2$. In some examples, the first therapeutic gas may be NO contained or delivered at a concentration of from about 500 ppm to about 1000 pm, and the second therapeutic gas may be air containing about 21% $O_2$ or pure $O_2$. In some examples, the first therapeutic gas may be NO contained or delivered at a concentration of from about 800 ppm to about 1000 ppm, and the second therapeutic gas may be air containing about 21% $O_2$ or pure $O_2$.

In some examples, the first therapeutic gas may be CO contained or delivered at a concentration of from about 100 ppm to about 250 ppm, and the second therapeutic gas may be air containing about 21% $O_2$ or pure $O_2$. In some examples, the first therapeutic gas may be CO contained or delivered at a concentration of from about 50 ppm to about 200 ppm, and the second therapeutic gas may be air containing about 21% $O_2$ or pure $O_2$.

In some examples, the first therapeutic gas may be a mixture of CO and NO, wherein the concentration of NO is from about 50 ppm to about 1000 ppm and the concentration of CO is from about 100 ppm to about 250 ppm, and the second therapeutic gas may be air containing about 21% $O_2$ or pure $O_2$. In some examples, the first therapeutic gas may be a mixture of CO and NO, wherein the concentration of NO is from about 50 ppm to about 250 ppm and the concentration of CO is from about 50 ppm to about 200 ppm, and the second therapeutic gas may be air containing about 21% $O_2$ or pure $O_2$. In some examples, the first therapeutic gas may be a mixture of CO and NO, wherein the concentration of NO is from about 500 ppm to about 1000 pm and the concentration of CO is from about 100 ppm to about 250 ppm, and the second therapeutic gas may be air containing about 21% $O_2$ or pure $O_2$. In some examples, the first therapeutic gas may be a mixture of CO and NO, wherein the concentration of NO is from about 800 ppm to about 1000 pm and the concentration of CO is from about 100 ppm to about 250 ppm, and the second therapeutic gas may be air containing about 21% $O_2$ or pure $O_2$.

The size, shape, and volume of the one or more chambers 120, 122, 130 may vary and the specific parameters may be selected based, in part, upon the applications in which it is to be used. The one or more chambers 120, 122, 130 may have an opening for interfacing with the topical area surrounding a wound site, which opening is fitted with one or more gas permeable membranes 110, 112. The size, shape and configuration of the gas delivery system, of one or more chambers 120, 122, 130, and of each opening may vary widely. Thus, a gas delivery system may have a circular, oval, square, rectangular, irregular or other cross sectional shape, and may be generally dome-shaped or have any other shape. Openings may likewise be of any shape. In one example, a suitable gas delivery system may be generally dome shaped and have a rectangular opening. The specific dimensions of the gas delivery system, of one or more chambers 120, 122, 130, and of each opening may likewise vary. In one example, an opening may have an area of about 1 $cm^2$-200 $cm^2$. The area may also be about 1-5 $cm^2$, 5-10 $cm^2$, 10-15 $cm^2$, 15-20 $cm^2$, 20-25 $cm^2$, 25-30 $cm^2$, 30-35 $cm^2$, 35-40 $cm^2$, 40-45 $cm^2$, 45-50 $cm^2$, 50-55 $cm^2$, 55-60 $cm^2$, 60-65 $cm^2$, 65-70 $cm^2$, 70-75 $cm^2$, 75-80 $cm^2$, 80-85 $cm^2$, 85-90 $cm^2$, 90-95 $cm^2$, 95-100 $cm^2$, 100-105 $cm^2$, 105-110 $cm^2$, 110-115 $cm^2$, 115-120 $cm^2$, 120-125 $cm^2$, 125-130 $cm^2$, 130-135 $cm^2$, 135-140 $cm^2$, 140-145 $cm^2$, 145-150 cm², 150-155 cm², 155-160 cm², 160-165 cm², 165-170 cm², 170-175 cm², 175-180 cm², 180-185 cm², 185-190 cm², 190-195 cm², 195-200 cm², and combinations thereof.

The pressure in the one or more chambers 120, 122, 130 may vary depending upon the application in which it is to be used. In some examples, the pressure in the one or more chambers 120, 122, 130 may be about 1.0-1.5 atm. The pressure may also be about 1.0-1.1, 1.1-1.2, 1.2-1.3, 1.3-1.4, 1.4-1.5 atm, and combinations thereof.

In some examples, the gas delivery system may comprise one or more ports. The gas delivery system 100 of FIGS. 1-6 further depict one or more ports 125, 135 for each chamber. Ports 125, 135 may be configured to allow the supply to and release of gases to the chamber. Ports 125, 135 are in operable communication with its respective chamber 120, 130. Ports 125, 135 may also be in operable communication with the surrounding atmosphere. This may allow, for example, a quantity of wound healing gas may be injected into one or more chambers 120, 122, 130 through the ports 125, 135 when a repeat gas treatment is required while the gas delivery system 100 is adhered to an area around a wound site. In some examples, ports 125, 135 may be configured to allow the continuous delivery of gases such that therapeutic gases are continuous supplied to one or more chambers through one port and removed through another port.

In some examples, the gas delivery system may comprise one or more additional ports. Ports 140 may be used for gaining access to a reservoir to insert or access devices, such as sensors, sample tissue or perform other operations. Thus, in some examples, one or more ports are provided for inserting or accessing sensors for monitoring exogenous gas and generated particle concentrations in a reservoir, above the wound site and/or within wound tissue. According to such examples, the sensors may be inserted through the port and into or proximate to the wound. In other such examples, the sensors are installed or integrated in the gas delivery system and are accessed through the port. In some examples, sensors for NO, CO, $O_2^-$, $O_2$, $ONOO^-$, or combinations thereof may be utilized for continuous monitoring of these molecules in one or more of the chambers, the gap above the wound and in the wound.

The gas delivery system 100 in FIGS. 1, 3, 4, and 5 further depict a port 140 that may allow a sensor 145 to be positioned at the wound site, or between the wound site and the at least one gas permeable membrane, wherein the sensor 145 may be configured to detect an amount of the first gas and second gas diffusing above the wound site and/or within wound tissue. The sensor may also be configured to control and/or monitor other parameters for optimal healing, including, for example, pressure, temperature, ONOO— concentration above the wound site and/or within wound tissue, NO/ONOO— ratio above the wound site and/or within wound tissue. In some examples, the sensor may be used to determine the presence of one or more therapeutic gases in one or more tissues. In some examples, the sensor may be configured to detect the concentration of one or more therapeutic gases on the surface of skin or a wound. In some examples, the sensor may be configured to be included within or operably connected to one or more chambers 120, 122, 130. In some examples, the sensor may be configured to be included within or operably connected to one or more gas permeable membranes 110, 112.

In the various embodiments, the gas delivery system 100 may be configured to deliver therapeutic gases in a controlled manner. For example, in some examples, a gas delivery system 100 may be associated with a sensor 145 that facilitates the delivery of therapeutic gases in a controlled manner. Such a configuration can allow for the concentration of one or more therapeutic gases within an area to be maintained within a selected range. Numerous concentrations of the one or more therapeutic gases may be maintained, which is detailed further below.

Many types of sensors may be used within the gas delivery system 100. Examples of such sensors include, but are not limited to, temperature sensors, pressure sensors (e.g., blood pressure, hydrostatic pressure), pulse rate sensors, clocks, bacterial contamination sensors, gas concentration sensors, and the like. In some examples, the sensor may detect one or more therapeutic gases through use of one or more electrodes. For example, a sensor may utilize an electrode that includes a single walled carbon nanotube to detect NO. In some examples, the sensor may include one or more transmitters. In some examples, the sensor may include one or more receivers. In some examples, the sensor may be configured to transmit one or more signals. In some examples, the sensor may be configured to receive one or more signals. In some examples, the sensor may be a nanosensor. In some examples, the sensor may be a porphyrinic nanosensor.

Methods

In addition to systems, also provided in various embodiments are methods for promoting wound healing, comprising (a) applying a provided gas delivery system to a wound site; and (b) delivering to the wound site, via the gas delivery system, one or more therapeutic gases selected from NO, CO, $O_2$, air, or combinations thereof, for a pre-determined period of time, wherein the one or more therapeutic gases are delivered such that a NO/ONOO⁻ ratio suitable for promoting wound healing is achieved at the wound site.

It is contemplated that the provided gas delivery systems may be used to treat various types of wounds. Examples include, but are not limited to, burns, incisions, excisions, lacerations, abrasions, punctures, penetrations, contusions, hematomas, crushing wounds, acute wounds, trauma wounds, chronic wounds, and ulcers. In some embodiments, the methods may be used to treat diabetes-associated wounds.

While there are many prevailing theories regarding potential underlying mechanisms responsible for the progression of wound healing, many of the mechanistic insights are still lacking. Without wishing to be bound by theory, it is believed that after about 4-5 min of ischemia, a massive generation of NO by endothelial (eNOS) and neuronal (nNOS) nitric oxide synthase occurs. After about 30 min of ischemia, NO production is diminished because an increased production of superoxide (mainly from disarranged NOS) results in production of ONOO— and a burst of other highly reactive radicals, including, for example, OH and $NO_2$. It is believed that a similar pattern of NO production as well as of $O_2^-$, $ONOO^-$ and OH generation is observed during wound healing. This process is followed by production of NO by inducible NOS (iNOS), and further increase in the production of oxidative species. High levels of oxidative species can trigger inflammation, edema, apoptosis and necrosis of the tissue, and can have a significant negative impact on the process of wound healing.

In light of the above, it is believed that preservation of the function of the constitutive nitric oxide synthase can prevent generation of oxidative species and can mollify the ischemic damage in the wounds and accelerate the process of wound healing. One possible way to preserve eNOS and nNOS is to limit the extensive NO production by these enzymes. To achieve this, the provided systems and methods utilize an exogenous supply of NO and/or CO to a hypoxic system of the wounds. It is believed that supplementation of exogenous NO inhibits NO production by eNOS or nNOS. The self-inhibitory roles of NO to cNOS and eNOS, as well as the inhibitory role of CO to cNOS, are well established. In addition to the inhibition process, it is believed that exogenous NO, CO, or both supplied to a wound by the provided systems and methods may also help to preserve the L-arginine pool, prevent disarrangement of NOS and production of superoxide by NOS, scavenge the $O_2^-$ radical from other sources than NOS sources, increase cGMP, prevent a generation of high concentration of ONOO$^-$, inhibit signaling of ONOO$^-$, increase vasorelaxation, and increase blood flow.

It is also believed that strong links exist between NO, CO, $O_2$ and wound angiogenesis, collagen accumulation and expression of endothelial growth factor. These factors, as well as other ischemia/reperfusion studies, led Applicant to the discovery that an increased level of topically applied NO, CO and $O_2$ can be highly beneficial in the acceleration of wound healing. Applicant found that the imbalance of [NO]/[ONOO$^-$] can be improved by topical delivery of exogenous NO to wound site. Without wishing to be bound by theory, it is believed that exogenously delivered NO may play the same role as endogenously generated NO by preserving NO bioavailability in the wound and maintaining a proper NO/ONOO$^-$ balance that promotes the healing process. Applicant has also discovered that wound size-dependent alterations in NOS homeostasis can be ameliorated by a strategy of gradual, diffusion controlled delivery of exogenous NO, CO or $O_2$ through gas permeable membranes.

In light of the above, provided are methods for promoting wound healing in a mammal (including, but not limited to, humans) by delivering therapeutic gases to a wound site such that a therapeutically effective NO/ONOO$^-$ ratio at the wound site is achieved. In some embodiments, this ratio may be pre-determined or determined during treatment. In some examples, the provided methods promote wound healing in a mammal by delivering therapeutic gases to a wound site so as to increase NO/ONOO$^-$ ratio at the wound site towards a NO/ONOO$^-$ ratio normally present in unwounded skin. In some examples, the methods promote wound healing in a mammal by delivering therapeutic gases to a wound site such that a NO/ONOO— ratio suitable for promoting wound healing is achieved at the wound site. In some examples, the methods promote wound healing in a mammal by delivering therapeutic gases to a wound in a diabetic person so as to increase NO/ONOO$^-$ ratio at the wound site towards a NO/ONOO$^-$ ratio present in a non-diabetic wound.

The NO/ONOO$^-$ ratio can quantify a level of oxidative/nitroxidative stress and NO/ONOO$^-$ imbalance. A high NO/ONOO$^-$ ratio may indicate a high concentration of bioavailable, cytoprotective NO and/or low levels of cytotoxic ONOO$^-$. The ratio can be expressed according to Equation 1 as follows:

$$K = \frac{[NO]}{[ONOO^-]} \quad (1)$$

where [NO] is the average nitric oxide concentration present in wound tissue and [ONOO$^-$] is the average peroxynitrite concentration present in wound tissue. In some examples, K may be determined by measuring the K value of unwounded skin. In some examples, K may have a value of at least about 0.5. In some examples, K may have a value of at least about 1. In some examples, K may have a value of at least about 2.

In one example, provided is a method for promoting wound healing in a mammal, comprising (a) applying to a wound site a provided gas delivery system, wherein said system comprises a gas reservoir comprising a first chamber for containing a first therapeutic gas and a second chamber for containing a second therapeutic gas; and at least one gas permeable membrane for controlling diffusion of a contained therapeutic gas from the reservoir to the wound site; (b) delivering to the first chamber a first therapeutic gas selected from NO, CO, or combinations thereof, such that the first therapeutic gas diffuses through the at least one gas permeable membrane to the wound site for a first pre-determined period of time; (c) delivering to the second chamber a second therapeutic gas selected from air, $O_2$, CO, or combinations thereof, such that the second therapeutic gas diffuses through the at least one gas permeable membrane to the wound site for a second pre-determined period of time. In such methods, the delivery of the first therapeutic gas to the wound site may occur before, after, or concurrent with the delivery of the second therapeutic gas to the wound site. In such methods, the first therapeutic gas and the second therapeutic gas are delivered such that a NO/ONOO$^-$ ratio suitable for promoting wound healing is achieved at the wound site.

In another example, the method generally comprises: (a) applying to the skin of a mammal, a gas delivery system comprising (i) a gas reservoir comprising a first chamber for containing a first therapeutic gas selected from NO, CO, or combinations thereof, and a second chamber for containing a second therapeutic gas selected from air, O2, CO, or combinations thereof, wherein the gas reservoir maintains a separation of gas in the first chamber from gas in the second chamber; (ii) a first gas permeable membrane for controlling diffusion of the first therapeutic gas to the wound site, the first gas permeable membrane operably connected to the first chamber; (iii) a second gas permeable membrane for controlling diffusion of the second therapeutic gas to the wound site, the second gas permeable membrane operably connected to the second chamber; (iv) at least one gasket for sealing the gas delivery system against skin surrounding the wound site, wherein the at least one gasket is operably connected to the first gas permeable membrane, the second gas permeable membrane, the gas reservoir, or combinations thereof; (v) a first gas port operably connected to the first chamber, the first gas port adapted to supply or remove the first therapeutic gas from the reservoir; and (vi) a second gas port operably connected to the second chamber, the second gas port configured to supply or remove the second therapeutic gas from the chamber; wherein the gas delivery system is disposed over the wound site thereby creating a gap between the wound site and the first and second gas permeable membranes; (b) delivering to the first chamber by the first gas port, a first therapeutic gas and allowing the first therapeutic gas to diffuse through the first gas permeable membrane to the wound site for a first pre-determined period of time; (c) delivering to the second chamber by the second gas port, a second therapeutic gas and allowing the second therapeutic gas to diffuse through the second gas permeable membrane to the wound site for a second pre-determined period of time.

In some examples, the first therapeutic gas and the second therapeutic gas may be delivered by the provide methods such that a pre-determined NO/ONOO— ratio at the wound site is achieved. In some examples, the first therapeutic gas and the second therapeutic gas may be delivered such that a NO/ONOO— ratio suitable for promoting wound healing is achieved at the wound site. In some examples, the first therapeutic gas and the second therapeutic gas may be delivered such that an increase in the NO/ONOO⁻ ratio towards a NO/ONOO⁻ ratio normally present in unwounded skin is observed.

In some examples, the methods allow exogenous NO and oxygen (pure or in air) to be topically delivered to the wound. In some examples, the methods allow exogenous CO and oxygen (pure or in air) to be topically delivered to the wound. In some examples, the methods allow exogenous NO and CO to be topically delivered to the wound. In some examples, NO, CO, and oxygen (pure or in air) are delivered to the wound. In some examples, one or more gases are delivered such that the concentration of NO achieved in the wound may be from about 5 nmol/L to about 50 nmol/L. Thus, the concentration of NO in the wound may be about 5-10, 10-15, 15-20, 20-25, 25-30, 30-35, 35-40, 40-45, or 45-50 nmol/L.

In some examples, the provided methods may maintain normal wound healing processes of the tissue. In some examples, the provided methods may accelerate the rate of wound healing relative to the normal processes of the tissue. In some examples, the provided methods may overcome impaired wound healing. In the various examples, it is contemplated that the methods may be used to treat open wounds, closed wounds, and combinations thereof. Thus, in some examples, it is contemplated that the methods may be used to treat surgical incisions, burns, and diabetes-related tissue injuries.

In the various examples, the treatment regime will vary greatly depending upon, among other factors, the size, severity, and type of wound being treated. In one example, daily treatment (i.e. delivery of one or more gases) time may range from about 5 minutes to about 24 hours, wherein treatment may be about 5-10, 10-15, 15-20, 20-25, 25-30, 30-35, 35-40, 40-45, 45-50, 50-55, 55-60 minutes; about 1, 2, 3, 4, 5, 6, 7, 8, 9, 10, 11, 12, 13, 14, 15, 16, 17, 18, 19, 20, 21, 22, 23, or 24 hours, or combinations thereof. In another example, one or more treatments per day may be utilized, wherein treatment may be 1, 2, 3, 4, 5, or more times per day. In a further example, treatment may be from 1-15 days, wherein treatment may be 1, 2, 3, 4, 5, 6, 7, 8, 9, 10, 11, 12, 13, 14, or 15 days. In some examples, a static treatment regime is provided where one or more gases is delivered in four to six treatments ranging from 15 mins to 1 hour within a 24-hour period. In other examples, a semi-continuous treatment regime is provided where one or more gases are continuously delivered over the course of eight hours to 20 hours, followed by exposure to air.

The provided methods may allow for significant decreased healing time of the wound, as compared to an untreated wound. For example, healing time may be decreased by as much as about 30%, 31%, 32%, 33%, 34%, 35%, 36%, 37%, 38%, 39%, 40%, 41%, 42%, 43%, 44%, 45%, 46%, 47%, 48%, 49%, and 50%.

In some examples, the methods of treatment comprise placing a provided gas delivery system above the wound (with membrane facing the wound) and sealing with a gel or double-sided adhesive layer of vinyl to the skin. The optional sensors may be inserted into the wound (or positioned between the wound and the at least one gas permeable membrane) and the concentration of NO, $O_2^-$, ONOO⁻, CO and $O_2$ measured, thereby allowing the mass transfer of NO and CO from the system to the wound to be monitored. Such mass transfer is controlled by the diffusion process through the membrane and gap above the wound and is based mainly on the concentration gradient (C0-C3, as illustrated in FIG. 7). Mass transport is characterized by measuring delivery rates of NO or CO alone, as well as a mixture of NO and CO in the presence or absence of air. The concentrations of NO, CO, $O_2$, and $NO_2$— (the end product of NO oxidation) are monitored continuously in different points of the diffusion pathway. The initial concentration of NO, CO, or both contained in the chamber will vary. These concentrations, as well as a small volume (order of few hundreds of cubic centimeters) of the other gases used, are believed to be below the levels that are considered to be toxic. CO and NO are believed to be dangerous when inhaled for over 30 min at concentrations higher than 1500 ppm for CO and 500 ppm (alternatively 5000 ppm) (for NO). Therefore, even under catastrophic conditions (like rupture of the gas delivery system) escape of these gases to the atmosphere should not produce a health hazard during practice of the method.

In some examples of methods, ultra high pure nitrogen (after passage through an $O_2$ trap) may be mixed with NO using controlled gas flow meters to obtain the desired NO gas concentration (for example, 10%) and the mixture pumped to one of the at least one chambers. Desired NO concentrations can range as previously described. For NO treatment, a second chamber may be filled with air (having, for example, 21% oxygen content) or pure oxygen. Alternatively, the second chamber may be filled with CO. For CO treatment, a first chamber may be filled with the desired concentration of CO and a second chamber filled with air or pure oxygen. For an oxygen-only treatment, only one chamber is needed and the gas permeable membrane may be removed but is nevertheless useful for a more controlled delivery. When air, or air and oxygen, or oxygen is to be used after NO treatment, the NO chamber should be purified with argon or nitrogen after the NO has been diffused.

In practice of the provided methods, the therapeutic gases may be administered by a clinician (doctor or other medical personnel) at a hospital or other medical facility in accordance with acceptable medical practice, taking into account the condition of the subject, including injection site condition, patient age, sex, body weight, and other determinable factors. The effective amount of therapeutic gas administered for purposes herein is thus determined by such considerations, as is known in the art, and is of sufficient amount to achieve the desired response, including but not limited to, an amount sufficient to achieve improvement in or elimination of the wound. The provided methods may be practiced on mammals, including humans.

EXAMPLES

The described embodiments will be better understood by reference to the following examples which are offered by way of illustration and which one of skill in the art will recognize are not meant to be limiting.

Example 1

The provided gas delivery system was refined using in vitro systems. For these experiments, primary cultures of endothelial cells, muscle cells as well as vessels, skin and tissue graft were used. The concentrations of NO, CO and $O_2$ and the concentration of oxidative species in the biological material were continuously monitored. The gas delivery system developed allows for a quantitative supply of NO, CO, $O_2$, or combinations thereof to be delivered to the wound.

Example 2

In vivo efficiency of the provided gas delivery system in the process of accelerating wound healing was also tested. For these experiments, a rat model of wound was studied. Indexes of post-ischemic injury included: morphometric analysis, tissue edema, using a laser rate of wound healing process, level of collagen, and breaking strength. These studies established roles of gaseous NO, CO and $O_2$ in decreasing susceptibility to ischemic vascular injury, decreased edema formation and accelerated wound healing. Using gas delivery systems of different shapes (e.g., circular or rectangular) and volumes (e.g., from about 10-500 $cm^3$), and having different areas (e.g., from 0.5-40 $cm^2$) of membranes, good results for wound healing in a single gas treatment were obtained using about 50-1000 ppm of NO, about 50-250 ppm CO, about 100% $O_2$, or combinations thereof. In some examples, good results were obtained using about 1000 ppm of NO, about 250 ppm CO, about 100% $O_2$, or combinations thereof.

Example 3

Provided methods and apparatus were tested on second degree burn wounds (normal and diabetic), excisional wounds (normal and diabetic), and surgical incisional wounds (normal and diabetic) in rat models. Various treatment protocols were evaluated and dose and time dependent studies were carried out on normal excisional wounds to determine the [NO] and [ONOO$^-$] release profile using exogenous NO and CO. The treatments resulted in a decreased wound healing time (versus control, untreated) by at least 20% for CO treatment, 30-50% for NO treatment as can be further seen in FIGS. 8, 9, and 10.

It is believed that gasotransmitters NO, $O_2$ and CO delivered locally to a wound site may influence the healing process via changing the NO/ONOO$^-$ balance. In diabetic and burn wounds, as compared to control normal wounds, measured levels of NO/ONOO$^-$ ratio are significantly imbalanced. As a result, there was a high formation of cytotoxic ONOO$^-$, which can contribute to wound healing impairment. Accordingly, wounds were exposed individually to either gaseous NO or CO using a modified gas delivery system surrounding an injured area. To determine the efficacy of gas therapy in restoring the NO/ONOO$^-$ balance, treated wounds were subjected to NO and ONOO$^-$ measurements. Also, eNOS and iNOS expression levels were determined using western blotting. Collagen formation and maturation, also wound contraction were investigated and compared to results of untreated wounds.

Type I Diabetes Model

Male Sprague-Dawley rats (body weight 400-450 g) were used for these studies, were kept in an animal care facility for 48 h at 21° C. in a temperature controlled room with a 12 h light/dark cycle and 30-70% air-changed humidity. Animals were allowed unlimited access to regular chow food and drinking water. Diabetes type I was induced in rats by injection of streptozotocin (STZ) (65 mg/kg in pH 4.5 citrate buffer, IP). To relieve the pain associated with the intraperitoneal streptozotocin injection, rats were first put under deep anesthesia by injecting (ketamine 50 mg/kg IM, xylazine 5 mg/kg, IM). Anesthesia levels were checked by corneal reflex and toe pinch, and sustained by additional injections of the ketamine and xylazine mixture. After 10 days of streptozotocin injections the blood glucose levels were measured to determine if the rats could be considered diabetic. If the blood glucose level was above 300 mg/dL, the rat was considered diabetic. Rats were fasted overnight before the glucose level was measured. After injecting anesthesia, the tip of the tail was sterilized by wiping it with 70% alcohol. Approximately 2 mm of the tail was cut off to withdraw a sample of blood (35 µl), and the tip was compressed for 45-60 seconds to stop the bleeding.

The diabetic rats were then anesthetized (if needed) with a mixture of ketamine (50 mg/kg I.M.) and xylazine (5 mg/kg I.M.) administered intraperitoneally. Once anesthetized, hair was removed from the rats' backs using an electric razor and the backs of the rat were subsequently wiped with a 70% ethyl alcohol swab. On either side of the midline of the rat's back, four excision wounds were made with a sterile about 5 mm in diameter Biopsy Punch (Miltex, Inc. York, Pa. cat#33-35). The resulting wounds were approximately 4 mm deep and were deprived of epidermis, dermis and subcutaneous fat. Immediately after wounding, the gasket of an exemplary gas delivery system as disclosed herein was bonded to the skin area surrounding each treated wound by means of a thin layer of Skin-Bond® Cement (Smith & Nephew Inc. Largo, Fla. 33773).

After the surgery and during the recovery period from anesthesia, rats were turned from side to side to avoid pulmonary edema and to ensure unobstructed breathing. The rats were transferred to cages lined with sterile drape and contained moist food. To minimize any stress associated with pain, the rats were injected subcutaneously with analgesic (Butorphanol 1-2 mg/kg) every four hours for a maximum period of 2 days. Additionally, 1-2 ml of warm sterile saline/100 g of body weight was injected subcutaneously during the recovery period to prevent dehydration. Once the rats were completely awake, they were placed in cages with free access to food and drinking water. During the postoperative care period, rats were monitored for signs of infection, or self inflicted trauma. Additionally food and water intake was monitored. The diabetic rats were subjected to treatment as described below.

Burn Wound Model

Similar to the rats used for the type I diabetic model, Rats were anesthetized with the mixture of ketamine 50 mg/kg IM and xylazine 5 mg/kg IM administered intraperitoneally. Anesthesia levels were maintained by additional injections of this mixture as needed. Each rat was allowed to breathe spontaneously. Hair was removed from the rats' backs and the backs of the rat were subsequently wiped with 70% ethanol. The standard rat burn model was used in which burns are produced by hot metal used as a heat source. A customized soldering iron was used to cause superficial dermal second-degree burns on. the backs of the rats. The soldering iron had a brass tip that was about 5 mm in diameter. It was heated to 80° C. and applied to the skin for 10 seconds, which caused second degree burns. Immediately after wounding, the gasket of an exemplary gas delivery system as disclosed herein was bonded to the skin area surrounding each treated wound by means of a thin layer of Skin-Bond® Cement (Smith & Nephew Inc. Largo, Fla. 33773). The animals were then transferred to individual cages for recovery. Rats received an analgesic (Butorphanol 1-2 mg/kg) injected subcutaneously every four hours for a maximum period of 2 days. To prevent dehydration, 1-2 ml of warm sterile saline/100 g of body weight was injected subcutaneously during the recovery period. The treatment procedures described in more detail below were executed in the same way for the burn wound model as the diabetic wound model. After a certain time period, the rats were again anesthetized using the procedure described above and the wounded skin was taken from the backs of these rats for analysis. Then rats were then euthanized with pentothal (150 mg/kg) injected intraperitoneally.

Gas Mixture Preparation

All gas mixtures were prepared and stored in HandyGrab Tedlar gas sampling bag with capacity of 0.6 liter (Zefon International, St. Petersburg, Fla., cat#HG-PP-06) prior to each treatment. Static mixing with nitrogen as a diluting gas was performed. To prepare nitric oxide mixtures in nitrogen, a sample of 1000 ppm nitric oxide in nitrogen (Airgas Specialty Gases, Chicago, Ill.) was drawn with a 50 cubic centimeters (cc) disposable medical syringe and then transferred to a Tedlar bag through an injection port. Then the appropriate volume of nitrogen (Airgas Inc., Radur, Pa.) was delivered to the bag that was controlled by a Riteflow® flowmeter (Bel-Art Products, Pequannock, N.J.). The same technique was used to prepare carbon monoxide mixtures in nitrogen, but a 1 cc disposable medical syringe was used to dosage pure carbon monoxide (Air Products and Chemicals Inc., Parkersburg, W. Va.). To calculate the concentrations of mixed gases, the following Equation 2 was applied:

$$C_{ppm}=V_c/(V_c+V_d)\times 10^6 \cdot ppm \qquad (2)$$

where $V_c$ is the target gas volume and $V_d$ is the dilutant volume.

For example, to prepare 400 cc of a 100 ppm nitric oxide mixture in nitrogen, 40 cc of 1000 ppm nitric oxide was diluted in 360 cc of nitrogen. Then the concentration of the particular gas in the mixture was measured by means of Gastec Pump (GasTec Corporation Fukaya, Japan, GV-100S) utilizing Gastec Gas Detection Tubes (No. 10 nitric oxide tubes and No. 1 L carbon monoxide tubes). Tubes that contain detecting reagents that are especially sensitive to a particular target gas produce a distinct layer of color change and concentration that can be read on the calibration scale.

Wound Treatment

Once the rats were prepared with a modified gas delivery system in place, 20 cm³ of nitrogen was purged through whole gas capsule to remove air. Then 20 cm³ of a therapeutic gas mixture was delivered in a medical syringe to a gas vent, and the gas vent was sealed. The wounds were exposed to gas mixtures for specified period of times (15 minutes to 1 hour). The treatment was repeated four times a day, while the rat was awake and fully ambulatory. Negative control wounds remained uncovered, allowing access of air to the wound site. Positive control wounds were exposed to pure nitrogen, which served as the diluting gas for every mixture prepared.

After a specified time interval (1 day, 3 days, 5 days, 7 days, 10 days), rats were again anesthetized with a mixture of ketamine (50 mg/kg I.M.) and xylazine (5 mg/kg I.M.). The gas delivery system was removed by applying few drops of Uni-Solve® (Smith & Nephew Inc. Largo, Fla. 33773), which enabled the removal of the gas delivery system from the skin. Wounds were then removed using a 6 mm in diameter biopsy punch (Miltex, Inc. York, Pa. cat #33-36). Removed wounds were immediately used to measure the NO and ONOO⁻ release or frozen in liquid nitrogen to be later subjected to hydroxyproline analysis and western blot analysis or embedded in TBS Tissue Frizzing Medium for histological analysis. After the wounded tissue was removed, the rats were euthanized by injecting pentothal at a dose of 150 mg/kg. The rats were then placed in cold storage in an animal care facility.

Referring to FIG. 7, depicted are changes in the burn wound area after treatment with either gNO or gCO. The wounds generally increased in sized and had gradual swelling the day after inducing burns. The changes in the wounds were monitored and treated for a 10 day time frame. The 2$^{nd}$ degree burn wounds were treated with either 1000 ppm NO or 250 ppm of CO gas mixtures for 15 minutes four times per day with at least an hour break between treatments. A marker 305 measuring 5 mm in diameter was placed next to each burn wound to show the size/area of the original generated burn wound. Over time, the burn wound size became swollen and increased in size. At day 3 the wound area treated with NO had increased by 76.3±4.2%, while the untreated burn wound area had more than doubled and rose by 102.1±6.7%. The increase in size and gradual swelling for all wounds ceased by day 5. The burn area size then declined for the next five days. By day 10, the size of the burn wounds treated with NO and CO were considerably smaller than in the control group (untreated burn wounds). The wound area of the control group had increased by roughly 169.0%+/−8.1% by day 10. The wound area of CO treated burns had increased by roughly 67.1%+/−3.5% by day 10. The wound area of NO treated burns had increased by roughly 58.0%+/−3.1% by day 10. Both treatment with gNO and gCO reduced swelling and accelerated burn healing process as compared to the untreated burn wound.

Figure 8:
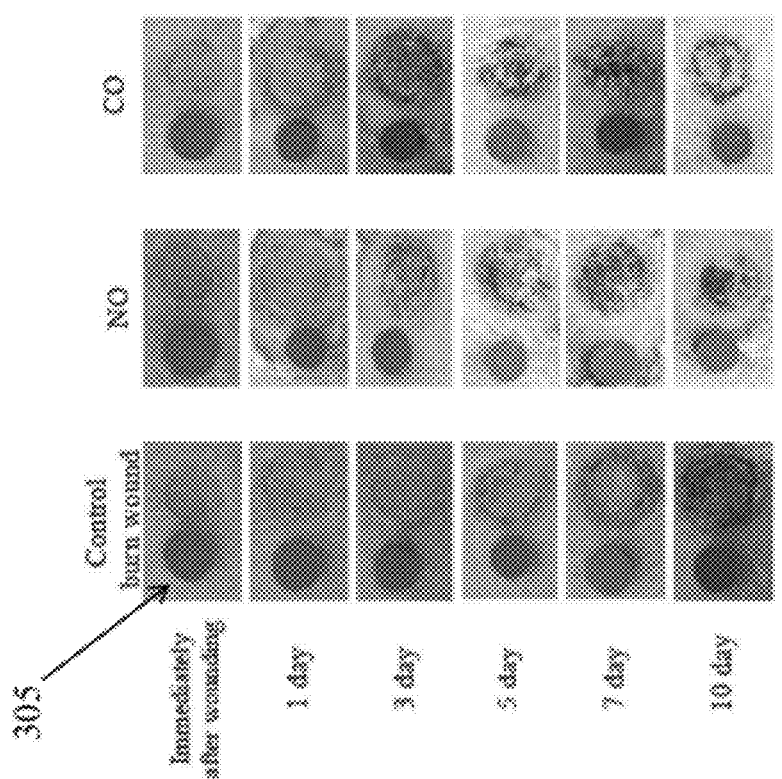
FIG. 8 depicts a comparison of the various stages of healing of a burn wound after treatment with therapeutic gases using a gas delivery system.

FIG. 8 depicts the general pattern of gCO and gNO treated diabetic excisional wound contraction compared to untreated diabetic excisional wound contraction. The diabetic type I excisional wounds were treated with either 1000 ppm NO or 250 ppm of CO gas mixtures for 15 minutes four times per day with at least an hour break between treatments. A marker 305 was placed next to each excisional wound to show the size/area of the original wound. In untreated wounds three days after injury, wound contraction resulted in a 5% wound size decrease as compared to the initial area. At day 5, CO treated wound area had shrunk to 82.6±3.7% of its initial area, whereas area of untreated wound area had shrunk to 84.1±4.2% of its initial area. The difference in wound size was most visible at day 7 when the NO treated wound area was 57.8±3.1% compared to 73.7±5.2% in untreated wounds. By day 10, the wound size had decreased to 46.6%+/−4.2% of its starting point. In comparison, wounds treated with NO were much smaller in size and by day 10 had decreased to 29.8%+/−2.5% of its starting point. Wounds treated with CO had decreased to 41.4%+/−2.8% of its starting point by day 10. There was nearly a 17% size difference between 10 day NO treated diabetic excisional wounds and untreated diabetic excisional wounds. The NO treatment accelerated wound contraction and stimulated wound repair. Exposing wounds to CO resulted in some influence on wound contraction, but the improvement was not as significant as was observed for NO treatment.

Figure 9:
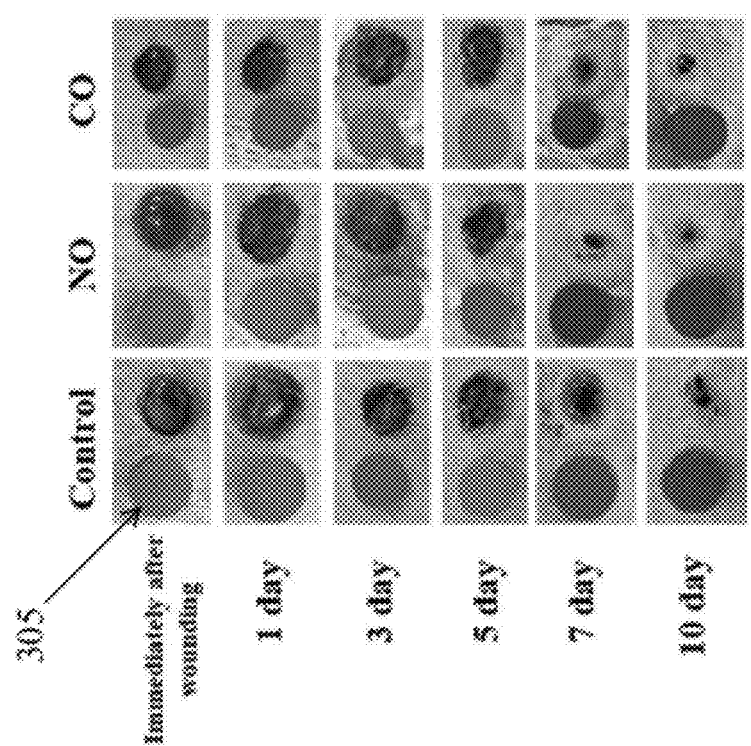
FIG. 9 depicts a comparison of the various stages of healing of a diabetic (type I) excision wound after treatment with therapeutic gases using a gas delivery system.

In FIG. 9, depicted are changes in wound size of a normal excisional wound after treatment with either NO or CO. The photographs were taken at 1, 3, 5, 7 and 10 days after wounding. Normal excisional wounds were treated with either 1000 ppm NO or 250 ppm of CO gas mixtures for 15 minutes four times per day with at least an hour break between treatments. A marker 305 was placed next to each excisional wound to show the size/area of the original wound. In general, the area of untreated control wounds gradually decreased as wound healing progressed in time. A very rapid drop in wound area was observed between the 5th and 7th day of healing. In untreated wounds one day after injury, wound contraction resulted in a nearly 10% wound size decrease as compared to the initial area. At day 10, the wound area/size had decreased to 31%+/−5% of its initial starting point. In comparison, wounds treated with NO showed significant healing improvement over time. At day 3, the area of the NO treated wound had shrunk to 58±4.9%, and the area of gCO treated wound had shrunk to 63±5.7%, whereas the area of untreated wound decreased to 81±6.1%. By day 10 NO treated wounds were much smaller than the untreated wounds and had decreased in size/area to 15%+/−3.8% of its starting point. Wounds treated with CO had decreased to 22.2%+/−3.3% of its starting point by day 10. Use of CO and NO accelerated wound contraction and resulted in a significant decrease in wound size.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and understood not to be limited to the details of structure and operation shown and described in the specification and drawings.

What is claimed is:

1. A system for controlled delivery of therapeutic gases to a wound site to promote wound healing, comprising:
    a gas reservoir comprising a first chamber for containing a first therapeutic gas comprising NO, and optionally further comprising CO; and a second chamber for containing a second therapeutic gas comprising $O_2$, and optionally further comprising CO; wherein the reservoir maintains a separation of a contained first therapeutic gas from a contained second therapeutic gas;
    at least one gas permeable membrane for controlling diffusion of a contained therapeutic gas from the reservoir to the wound site, the at least one gas permeable membrane operably connected to the gas reservoir;
    wherein the system maintains a space between the wound site and the at least one gas permeable membrane when the system is applied to a wound site; and
    wherein the system delivers, when the system is applied to a wound site, the contained therapeutic gases such that a NO/ONOO$^-$ ratio suitable for promoting wound healing is achieved at the wound site.

2. A system of claim 1, further comprising at least one gas sensor capable of determining an amount of one or more of NO, CO, $O_2^-$, $O_2$, and ONOO$^-$ at the wound site.

3. A system of claim 2, wherein the at least one gas sensor is positioned between the wound site and the at least one gas permeable membrane when the system is applied to a wound site.

4. A system of claim 1, adapted to deliver the first therapeutic gas before, after, or concurrently with the second therapeutic gas.

5. A system of claim 4, adapted to deliver the first and second therapeutic gases such that the NO/ONOO$^-$ ratio at the wound site increases.

6. A system for controlled delivery of therapeutic gases to a wound site to promote wound healing, comprising:
    a gas reservoir comprising a first chamber for containing a first therapeutic gas comprising NO and optionally further comprising CO; and a second chamber for containing a second therapeutic gas comprising $O_2$ and optionally further comprising CO; wherein the reservoir maintains a separation of a contained first therapeutic gas from a contained second therapeutic gas;
    a first gas permeable membrane for controlling diffusion of a contained first therapeutic gas from the reservoir to the wound site, the first gas permeable membrane operably connected to the first chamber;
    a second gas permeable membrane for controlling diffusion of a contained second therapeutic gas from the reservoir to the wound site, the second gas permeable membrane operably connected to the second chamber;
    at least one gasket for sealing the system against skin surrounding the wound site, the at least one gasket operably connected to the first gas permeable membrane, the second gas permeable membrane, the gas reservoir, or combinations thereof;
    a first gas port operably connected to the first chamber, the first gas port adapted to supply a first therapeutic gas to the first chamber when connected to first therapeutic gas source, to remove a contained first therapeutic gas from the first chamber, or both;
    a second gas port operably connected to the second chamber, the second gas port adapted to supply a second therapeutic gas to the second chamber when connected to second therapeutic gas source, to remove a contained second therapeutic gas from the second chamber, or both;
    wherein the system maintains a space between the wound site and the first and second gas permeable membranes when the system is applied to a wound site; and
    wherein the system delivers, when the system is applied to a wound site, the contained therapeutic gases such that a NO/ONOO$^-$ ratio suitable for promoting wound healing is achieved at the wound site.

7. A system of claim 6, further comprising at least one gas sensor capable of determining the amount of one or more of NO, CO, $O_2^-$, $O_2$, and ONOO$^-$ at the wound site;
    wherein the at least one gas sensor is positioned between the wound site and the first and second gas permeable membranes when the system is applied to a wound site.

8. A system of claim 6, adapted to deliver the first therapeutic gas before, after, or concurrently with the second therapeutic gas.

9. A system of claim 8, adapted to deliver the first and second therapeutic gases such that the NO/ONOO$^-$ ratio at the wound site increases.

10. A method for promoting wound healing, comprising:
    (a) applying to a wound site of a mammal, a gas delivery system comprising:
        a gas reservoir comprising a first chamber for containing a first therapeutic gas;
        and a second chamber for containing a second therapeutic gas; wherein the reservoir maintains a separation of a contained first therapeutic gas from a contained second therapeutic gas;

at least one gas permeable membrane for controlling diffusion of a contained therapeutic gas from the reservoir to the wound site, the at least one gas permeable membrane operably connected to the gas reservoir, wherein the gas delivery system maintains a space between the wound site and the at least one gas permeable membrane when the gas delivery system is applied to a wound site;

(b) delivering to the first chamber a first therapeutic gas comprising NO, and optionally further comprising CO, such that the first therapeutic gas diffuses through the at least one gas permeable membrane to the wound site for a first pre-determined period of time;

(c) delivering to the second chamber a second therapeutic gas comprising $O_2$ and optionally further comprising CO, such that the second therapeutic gas diffuses through the at least one gas permeable membrane to the wound site for a second pre-determined period of time;

wherein the delivery of the first therapeutic gas to the wound site occurs before, after, or concurrent with the delivery of the second therapeutic gas to the wound site; and wherein the first therapeutic gas and the second therapeutic gas are delivered such that a NO/ONOO$^-$ ratio suitable for promoting wound healing is achieved at the wound site.

11. A method of claim 10, comprising monitoring the amount of one or more of NO, CO, $O_2^-$, $O_2$, and ONOO$^-$ at the wound site; wherein the gas delivery system further comprises at least one gas sensor capable of determining the amount of one or more of NO, CO, $O_2^-$, $O_2$, and ONOO$^-$ at the wound site.

12. A method of claim 10, wherein CO is delivered to the wound site before, after, or concurrent with delivery of NO to the wound site.

13. A method of claim 12, wherein NO is delivered at a concentration of from 50 ppm to 1000 ppm, and CO is delivered at a concentration of from 50 ppm to 250 ppm.

14. A method of claim 10, wherein NO is delivered to the wound site before or after delivery of $O_2$ or air to the wound site.

15. A method of claim 14, wherein NO is delivered at a concentration of from about 50 ppm to about 1000 ppm.

16. A method of claim 10, wherein CO is delivered to the wound site before, after, or concurrent with delivery of $O_2$ or air to the wound site.

17. A method of claim 10, wherein a NO/CO mixture is delivered to the wound site before or after delivery of $O_2$ or air to the wound site.

18. A method of claim 10, wherein the first and second therapeutic gases are delivered such that the NO/ONOO— ratio at the wound site increases.

19. A method of claim 18, wherein the therapeutic gases are delivered such that a wound site concentration of NO from about 5 nmol/L to 50 nmol/L is achieved.

20. A method of claim 10, wherein the wound is selected from burns, incisions, excisions, lacerations, abrasions, punctures, penetrations, contusions, hematomas, crushing wounds, acute wounds, trauma wounds, chronic wounds, and ulcers.

21. A method of claim 20, wherein the mammal is diabetic.

* * * * *